US012178417B2

(12) United States Patent
Cox, Jr. et al.

(10) Patent No.: US 12,178,417 B2
(45) Date of Patent: Dec. 31, 2024

(54) DEVICES AND METHODS FOR UMBILICAL CORD PROCESSING

(71) Applicant: BOARD OF REGENTS OF THE UNIVERSITY OF TEXAS SYSTEM, Austin, TX (US)

(72) Inventors: Charles S. Cox, Jr., Houston, TX (US); Brijesh S. Gill, Houston, TX (US); Kevin Aroom, Houston, TX (US); Tushar Sharma, Houston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 18/332,710

(22) Filed: Jun. 10, 2023

(65) Prior Publication Data

US 2023/0320709 A1    Oct. 12, 2023

Related U.S. Application Data

(62) Division of application No. 16/644,367, filed as application No. PCT/US2018/049453 on Sep. 5, 2018, now Pat. No. 11,723,635.

(60) Provisional application No. 62/554,203, filed on Sep. 5, 2017.

(51) Int. Cl.
*A61B 10/02* (2006.01)
*A61B 17/00* (2006.01)
*A61B 17/32* (2006.01)
*A61B 10/00* (2006.01)

(52) U.S. Cl.
CPC .... *A61B 17/00008* (2013.01); *A61B 10/0233* (2013.01); *A61B 17/32* (2013.01); *A61B 10/0096* (2013.01); *A61B 2010/0208* (2013.01); *A61B 2017/00398* (2013.01); *A61B 2017/320064* (2013.01)

(58) Field of Classification Search
CPC . A61B 17/00008; A61B 17/142; A61B 17/32; A61B 2017/0208; A61B 2017/320056; A61B 2017/32006; A61B 10/0233; A61K 35/51; B26D 1/06; B26D 1/065
See application file for complete search history.

(56) References Cited

U.S. PATENT DOCUMENTS

| | | | |
|---|---|---|---|
| 1,275,414 | A | 8/1918 | Forbes |
| 2,630,148 | A | 3/1953 | Ferguson |
| 4,255,858 | A | 3/1981 | Getts |
| 4,949,464 | A | 8/1990 | Adomatis |
| 5,000,419 | A | 3/1991 | Palmer et al. |

(Continued)

FOREIGN PATENT DOCUMENTS

| | | |
|---|---|---|
| CN | 2019/68745 | 9/2011 |
| WO | WO/2008/060037 | 5/2008 |
| WO | WO/2011/101834 | 8/2011 |

OTHER PUBLICATIONS

U.S. Appl. No. 15/449,085, filed Sep. 7, 2017, Cox et al.

(Continued)

*Primary Examiner* — Martin T Ton
(74) *Attorney, Agent, or Firm* — Parker Highlander PLLC

(57) ABSTRACT

Devices and methods for extraction and processing of *substantia gelatinea funiculi umbilicalis* (Wharton's Jelly) from an umbilical cord.

14 Claims, 28 Drawing Sheets

(56) References Cited

U.S. PATENT DOCUMENTS

| | | | |
|---|---|---|---|
| 5,205,043 | A | 4/1993 | Batt et al. |
| 5,522,294 | A * | 6/1996 | Krumdieck ............... G01N 1/06 |
| | | | 83/915.5 |
| 5,561,909 | A | 10/1996 | Berg et al. |
| 5,690,646 | A * | 11/1997 | Gruenberg ............. A61B 5/417 |
| | | | 600/573 |
| 5,919,702 | A | 7/1999 | Purchio et al. |
| 6,302,406 | B1 | 10/2001 | Ventura |
| 7,146,895 | B2 | 12/2006 | Kong |
| 7,309,055 | B1 | 12/2007 | Spiegel et al. |
| 8,893,995 | B2 | 11/2014 | Taghizadeh |
| 8,900,863 | B2 | 12/2014 | Kallis et al. |
| 9,012,222 | B2 | 4/2015 | Taghizadeh |
| 11,109,888 | B1 | 9/2021 | Zahid |
| 2001/0054429 | A1 | 12/2001 | Witter |
| 2003/0112594 | A1 | 7/2003 | Smith |
| 2005/0197596 | A1 * | 9/2005 | Bellucci ........... A61B 5/150068 |
| | | | 600/573 |
| 2008/0082060 | A1 | 4/2008 | Ogata et al. |
| 2008/0118477 | A1 | 5/2008 | Christopherson |
| 2009/0120957 | A1 | 5/2009 | Phillips |
| 2011/0151556 | A1 | 6/2011 | Kallis et al. |
| 2013/0072951 | A1 | 3/2013 | Trezza et al. |
| 2013/0183273 | A1 | 7/2013 | Taghizadeh |
| 2014/0120615 | A1 | 5/2014 | Fong et al. |
| 2017/0252380 | A1 * | 9/2017 | Cox, Jr. ............... C12N 5/0605 |
| 2017/0253280 | A1 | 9/2017 | Cox |

OTHER PUBLICATIONS

Chang, Zhengqi, et al. "Umbilical cord wharton's jelly repeated culture system: a new device and method for obtaining abundant mesenchymal stem cells for bone tissue engineering." *PloS one* 9.10 (2014): e110764.

Hou, Tianyong, et al. "Umbilical cord Wharton's Jelly: a new potential cell source of mesenchymal stromal cells for bone tissue engineering." *Tissue Engineering Part A* 15.9 (2009): 2325-2334.

Hu, Ying, et al. "Wharton's jelly mesenchymal stem cells differentiate into retinal progenitor cells." *Neural regeneration research* 8.19 (2013): 1783.

International Preliminary Report on Patentability issued in corresponding PCT Application No. PCT/US2018/049453, mailed on Mar. 19, 2020.

International Search Report and Written Opinion issued in corresponding PCT Application No. PCT/US2018/049453 9, mailed on Dec. 27, 2018.

International Search Report and Written Opinion issued in International Application No. PCT/US2017/020664, dated Jul. 19, 2017.

Kamolz, Lars-Peter, Maike Keck, and Cornelia Kasper. "Wharton's jelly mesenchymal stem cells promote wound healing and tissue regeneration." *Stem cell research & therapy* 5.3 (2014): 62.

Kim, Dae-Won, et al. "Wharton's jelly-derived mesenchymal stem cells: phenotypic characterization and optimizing their therapeutic potential for clinical applications." *International journal of molecular sciences* 14.6 (2013): 11692-11712.

Leeb, Christian, et al. "Promising new sources for pluripotent stem cells." *Stem Cell Reviews and Reports* 6.1 (2010): 15-26.

Lu, Lu-Lu, et al. "Isolation and characterization of human umbilical cord mesenchymal stem cells with hematopoiesis-supportive function and other potentials." *haematologica* 91.8 (2006): 1017-1026.

Montanucci, Pia, et al. "New simple and rapid method for purification of mesenchymal stem cells from the human umbilical cord Wharton jelly." *Tissue Engineering Part A* 17.21-22 (2011): 2651-2661.

Ribeiro, Jorge, et al. "Perspectives of employing mesenchymal stem cells from the Wharton's jelly of the umbilical cord for peripheral nerve repair." *Int Rey Neurobiol* 108 (2013): 79-120.

Supplementary Partial European Search Report issued in European Application No. 17760900.5, dated Sep. 30, 2019.

Taghizadeh, R. R., K. J. Cetrulo, and C. L. Cetrulo. "Wharton's Jelly stem cells: future clinical applications." *Placenta* 32 (2011): S311-S315.

Zhao, Guifang, et al. "Large-scale expansion of Wharton's jelly-derived mesenchymal stem cells on gelatin microbeads, with retention of self-renewal and multipotency characteristics and the capacity for enhancing skin wound healing." *Stem cell research & therapy* 6.1 (2015): 38.

* cited by examiner

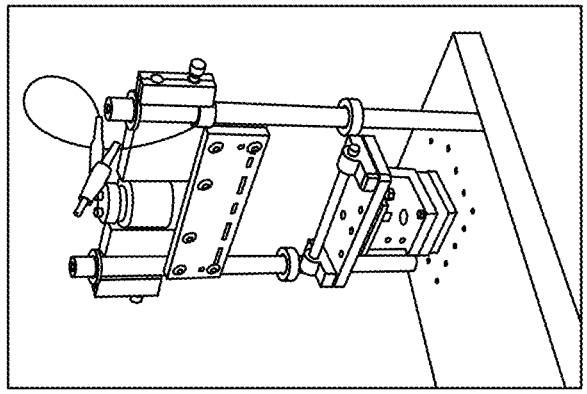
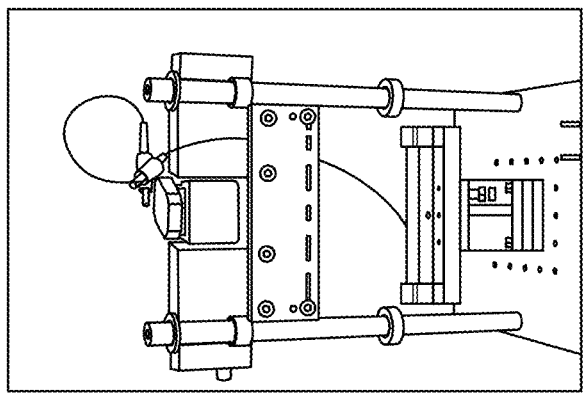
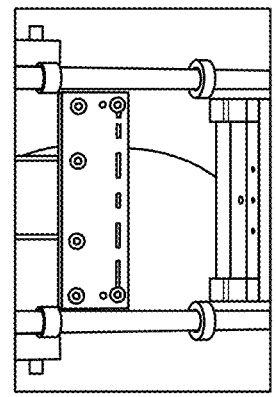
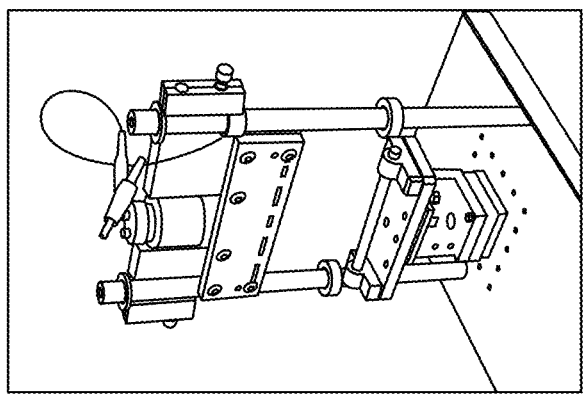
FIG. 9

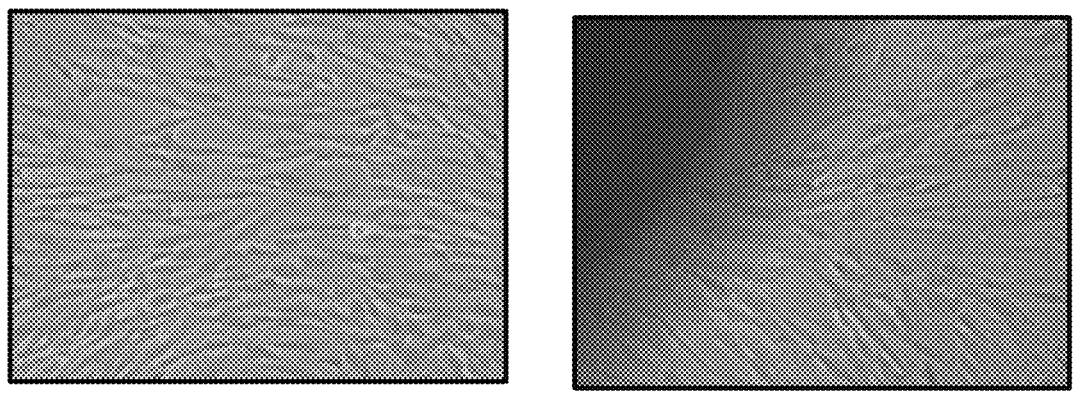
FIG. 16
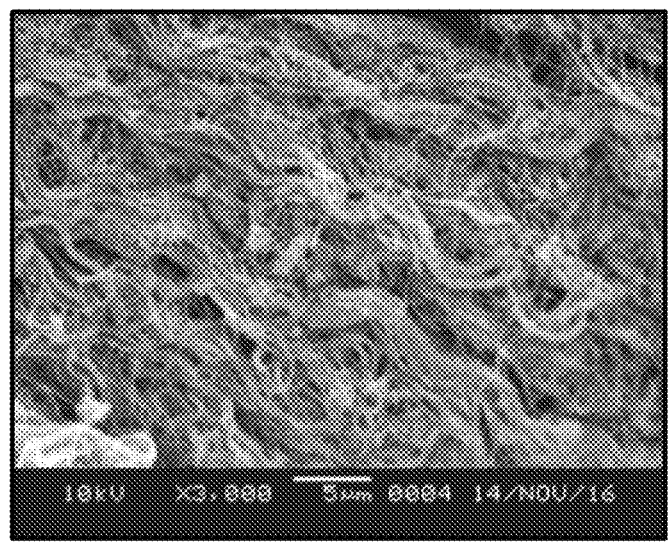
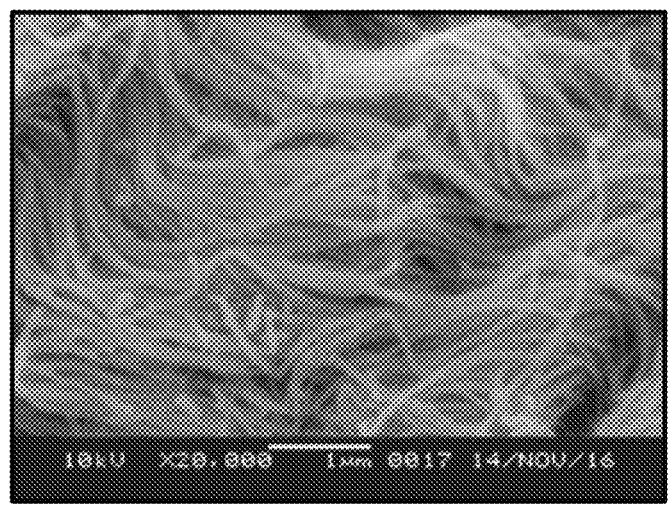
FIG. 17

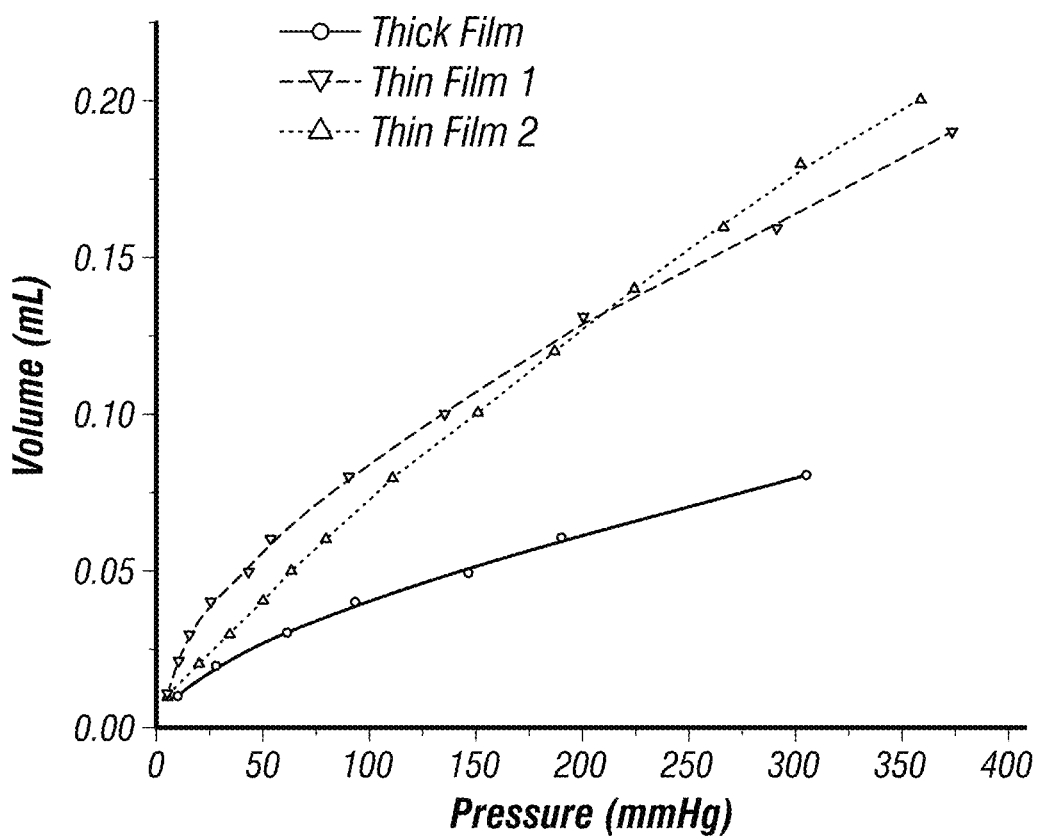
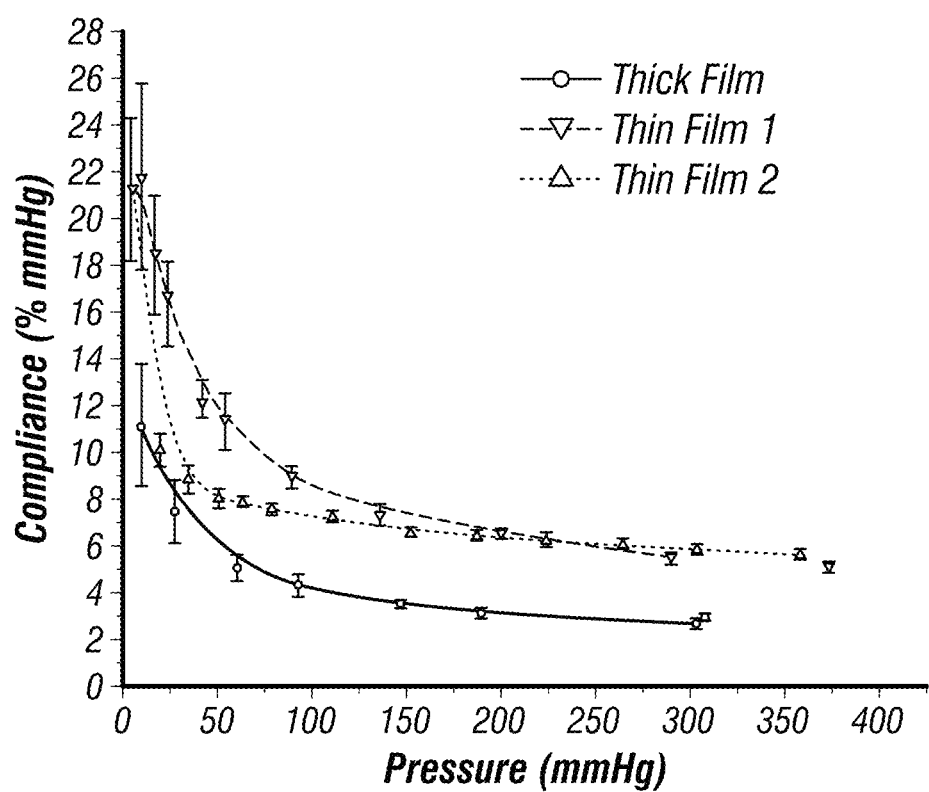
FIG. 20

DEVICES AND METHODS FOR UMBILICAL CORD PROCESSING

CROSS-REFERENCE TO RELATED APPLICATIONS

This application is a divisional of U.S. patent application Ser. No. 16/644,367, filed Mar. 4, 2020, as a national phase application under 35 U.S.C. § 371 of International Application No. PCT/US2018/049453, filed Sep. 5, 2018, which claims priority to U.S. Provisional Patent Application Ser. No. 62/554,203 filed Sep. 5, 2017, the contents of each of which are incorporated herein by reference.

BACKGROUND OF THE INVENTION

I. Field of the Invention

Embodiments of the present disclosure relate to devices, kits and methods for processing umbilical cords, in particular, the extraction of Wharton's Jelly from umbilical cords.

II. Background of the Invention

Cleft lip and cleft palate (CLP) is the most common birth defect in the United States, affecting more than 2,650 children born each year according to the Centers for Disease Control and Prevention. Cleft palate is the gap in the bony region above the front teeth which causes an opening between the mouth and the nasal cavity leading to insufficient support for front teeth and facial development.

The accepted standard treatment for cleft palate is autologous bone grafting, which provides a stable repair but is invasive and can be followed by potential complications of graft exposure and loss. In addition, autologous bone grafting is subject to donor site morbidity including infection, long-term pain and/or nerve damage that lead to the need of additional surgeries. Another strategy based on using biomaterials seeded with bone marrow (BM) stem cells has proven promising, but BM harvest is too invasive to use in CLP repair in newborns. Accordingly, alternative strategies are needed. In this context, *substantia gelatinea funiculi umbilicalis* (i.e. Wharton's Jelly) represents a natural biomaterial of great potential. Native Wharton's Jelly (nWJ) is the connective tissue of the umbilical cord, and it is composed of a network of proteoglycans and collagen embedded with perinatal stem cells, a bridge between embryonic and adult stem cells without the limitations of either. It is a natural "tissue engineering" construct that provides a scaffold derived from the recipient's own molecules, naturally seeded with the recipient's own stem cells, and is thus immunologically inert. Since nWJ is typically discarded as post-delivery medical waste, its use does not pose ethical concerns and its harvest is completely non-invasive. The inventors of the inventions disclosed herein have shown in an alveolar defect model representative of cleft palate surgery in the rat, that inclusion of nWJ in the alveolar pocket at the time of palate repair enhances bone growth and accelerates healing, proving to be an adjunct of great potential to orofacial cleft repair. The success of this approach would represent a paradigm shift in the treatment of CLP patients, significantly anticipating the timing of surgical correction and reducing or eliminating the need for subsequent bone grafting. Furthermore, patches obtained with the embodiments described herein have the potential to be used in several autologous implants or allograft in which barrier function can be augmented, such as abdominal wall defects, congenital diaphragmatic hernia, and urological procedures.

SUMMARY OF THE INVENTION

Certain embodiments include an apparatus for processing an umbilical cord, where the apparatus comprises a handle, a tapered rod coupled to the handle, and a blade coupled to the handle. In particular embodiments, the tapered rod is configured for insertion into a lumen of a blood vessel in an umbilical cord. In specific embodiments the blade comprises a cutting edge, and the tapered rod and blade are positioned such that a radial space exists between the tapered rod and the cutting edge of the blade. In some embodiments, the blade cuts the umbilical cord along a length of the umbilical cord when the tapered rod is inserted into the lumen of the blood vessel in the umbilical cord, and the blade does not cut the blood vessel in umbilical cord when the tapered rod is inserted into the lumen of the blood vessel in the umbilical cord.

Certain embodiments include an apparatus for processing an umbilical cord, where the apparatus comprises: a base plate assembly, where the base plate assembly has a planar surface; a bar coupled to the base plate assembly, where the bar is spaced from the planar surface such that a first gap exists between the bar and the planar surface; a motor coupled to the base plate assembly, and a reciprocating blade coupled to the motor, where the motor comprises a shaft with an eccentric pinion, and the shaft with the eccentric pinion is generally perpendicular to the bar, the reciprocating blade comprises a cutting edge that is parallel to the bar, and a second gap exists between the cutting edge and the bar.

In particular embodiments, the base plate assembly comprises a cover plate coupled to a base plate. In some embodiments, the first gap is 0.1 mm and 20.0 mm, and in specific embodiments, is approximately 4 mm. In certain embodiments, the second gap is between 0.1 mm and 20 mm, and in particular embodiments, is approximately 1.0 mm. In some embodiments, the bar comprises a flat surface proximal to the cutting edge of the reciprocating blade. In specific embodiments, the bar is configured to snap into the base plate assembly when the bar is coupled to the base plate assembly.

Certain embodiments further comprise a plurality of bars, where each bar in the plurality of bars is configured to couple to the base plate assembly, and where each bar in the plurality of bars is configured to provide a different gap spacing between each bar and the planar surface when coupled to the base plate assembly. In particular embodiments, the reciprocating blade is coupled to the motor via a blade carrier. In some embodiments, the blade carrier comprises a slot, and the eccentric pinion of the motor engages the slot. In specific embodiments, the motor and the reciprocating blade are contained in a motor and blade assembly.

In certain embodiments, the motor and blade assembly comprises: a motor housing configured to contain the motor; a blade carrier configured to contain the reciprocating blade; and a blade cover configured to couple to the motor housing and contain the blade carrier and the blade. In particular embodiments, the motor and blade assembly is configured to be coupled to the base plate assembly and de-coupled from the base plate assembly without the use of tools. In some embodiments, the motor and blade assembly is configured to couple to the base plate assembly via one or more spring-loaded plungers. In specific embodiments, the one or more spring-loaded plungers are configured to engage a groove in the motor housing when the motor and blade assembly is coupled to the base plate assembly.

Certain embodiments further comprise a release handle coupled to the one or more spring-loaded plungers. In particular embodiments, the one or more spring-loaded plungers are configured release from the groove in the motor housing when the release handle is pulled in a direction away from the groove in the motor housing. Some embodiments, further comprise sliding shafts between the motor housing and the blade cover.

Certain embodiments include a method of harvesting a patch from an umbilical cord, where the method comprises: obtaining an apparatus as disclosed herein; inserting one end of an umbilical cord between the planar surface of the base plate and the bar; wrapping the umbilical cord around the bar; pulling the first end of the umbilical cord away from the bar; and engaging the reciprocating blade with the umbilical cord to cut a patch from the umbilical cord.

In particular embodiments, engaging the umbilical cord comprises operating the motor to move the reciprocating blade back and forth above the bar. In some embodiments, the bar exerts a frictional resistance force when the first end of the umbilical cord is pulled away from the bar. Specific embodiments, further comprise adjusting the first gap between the bar and the planar surface.

In certain embodiments, adjusting the first gap between the bar and the planar surface comprises replacing the bar coupled to the base plate assembly with a different bar that is spaced from the planar surface a different gap than the first gap. In particular embodiments, the patch comprises Wharton's Jelly and amnion. In some embodiments, the patch does not comprise umbilical arteries, and in specific embodiments, the umbilical cord has been processed to remove a blood vessel before harvesting the patch from the umbilical cord.

In certain embodiments, the umbilical cord has been processed by: obtaining a device comprising a handle coupled to a tapered rod and coupled to a blade, wherein the blade is spaced apart from the tapered rod; inserting the tapered rod into a lumen of the blood vessel of the umbilical cord; and cutting the umbilical cord along a length of the umbilical cord with the blade.

In particular embodiments, the tapered rod and blade are positioned such that a radial space exists between the tapered rod and the blade; the blade cuts the umbilical cord along a length of the umbilical cord when the tapered rod is inserted into the lumen of the blood vessel in the umbilical cord; and the blade does not cut the blood vessel in umbilical cord when the tapered rod is inserted into the lumen of the blood vessel in the umbilical cord.

Specific embodiments further comprise compressing the blood vessel of the umbilical cord on the tapered rod without cutting the blood vessel of the umbilical cord. Certain embodiments further comprise pulling the umbilical cord along the tapered rod and toward the handle. Particular embodiments further comprise using forceps to pull the umbilical cord along the tapered rod and toward the handle. In specific embodiments, the blood vessel of the umbilical cord is an umbilical vein.

Certain embodiments include a method of processing an umbilical cord, where the method comprises obtaining an apparatus as disclosed herein (including for example, an apparatus as described in the immediately preceding paragraph). In particular embodiments, the method comprises inserting the tapered rod of the apparatus into a lumen of a blood vessel of an umbilical cord; cutting the umbilical cord along a length of the umbilical cord with the blade of the apparatus; and compressing the blood vessel of the umbilical cord on the tapered rod without cutting the blood vessel of the umbilical cord.

Some embodiments further comprise pulling the umbilical cord along the tapered rod and toward the handle. Specific embodiments further comprise using forceps to pull the umbilical cord along the tapered rod and toward the handle. In certain embodiments, the blood vessel of the umbilical cord is an umbilical vein.

Exemplary embodiments include an apparatus for processing an umbilical cord, where the apparatus comprises: a base plate, where the base plate assembly has a planar surface; a receptacle coupled to the base plate, where the receptacle comprises a lid; and a motor coupled to the base plate, and further where: the motor comprises a shaft with an eccentric pinion; and the shaft with the eccentric pinion is generally perpendicular to the lid; and a reciprocating blade coupled to the motor, and still further where: the reciprocating blade comprises a cutting edge that is parallel to the lid; and a gap exists between the cutting edge and the lid.

In certain embodiments, the gap is approximately 1.0 mm. In particular embodiments the reciprocating blade is coupled to the motor via a blade carrier. In some embodiments the blade carrier comprises a slot, and the eccentric pinion of the motor engages the slot. In specific embodiments the motor and the reciprocating blade are coupled to a chassis. In certain embodiments the base plate supports a pair of vertical members, the chassis is coupled to the pair of vertical members, and the chassis can be adjusted in a direction perpendicular to the lid. Some embodiments further comprise a spring-loaded retaining mechanism configured to couple the receptacle to the base plate.

Particular embodiments include an apparatus for processing an umbilical cord, where the apparatus comprises: a base plate; a motor coupled to the base plate; a reciprocating blade coupled to the motor; and a bar coupled to the base plate.

Certain embodiments include a method of processing an umbilical cord, where the method comprises obtaining an apparatus as disclosed herein (including for example an apparatus as described in the immediately preceding paragraphs). In certain embodiments, the umbilical cord comprises Wharton's Jelly, amnion and umbilical arteries before processing. In particular embodiments, the patch comprises Wharton's Jelly and amnion, and in specific embodiments, the patch does not comprise umbilical arteries.

Accordingly, the embodiments of the present disclosure provide for devices, kits and methods of processing umbilical cords to extract *substantia gelatinea funiculi umbilicalis* (i.e. Wharton's Jelly).

In yet a further embodiment, the invention provides an isolated pluripotent cell composition comprising a Wharton's Jelly having substantially intact tissue structural elements produced by a method according to the embodiments and aspects described herein. In some particular aspects, the Wharton's Jelly exhibits a stiffness of between about 0.01 kPa to 10 kPa.

In still yet a further embodiment, there is provided an isolated pluripotent cell composition comprising a Wharton's Jelly having substantially intact tissue structural elements, wherein the Wharton's Jelly is thixotropic and/or exhibits a stiffness of between about 0.01 kPa to 10 kPa.

In further aspects, the Wharton's Jelly exhibits a stiffness of between about 0.02 kPa to 8 kPa. In some specific aspects, the Wharton's Jelly exhibits a stiffness of greater than 0.1, 0.2, 0.3, 0.4, 0.5, 0.6, 0.7, 0.8, 0.9 or 1.0 kPa. In other aspects, the Wharton's Jelly exhibits a stiffness of between about 0.05 kPa to 5 kPa; 0.1 kPa to 5 kPa; or 0.5 kPa to 3 kPa. In certain aspects, the Wharton's Jelly may be thixotropic.

In additional aspects, the cell composition is frozen. In other aspects, the cell composition has been subjected to one freeze/thaw cycle. In particular aspects, the cell composition has been tested and determined to be free of pathogenic bacteria, viruses and/or fungi. In certain aspects, at least about 80% of the pluripotent cells in the Wharton's Jelly are viable cells. In some specific aspects, the isolated pluripotent cell composition further comprises a preservative or stabilizing reagent.

In yet still a further embodiment, the invention provides a method of treating a subject in need thereof comprising administering to the subject an effective amount of a composition according to the embodiments and aspects described herein. In some aspects, the composition is administered by injection. In other aspects, the composition is administered by surgical implantation. In certain aspects, the subject has a tissue deficit and the composition is administered at the site of the deficit. In a specific aspect, the subject has a cleft palate. In another aspect, the subject has a wound. In additional aspects, the cells in the composition are allogenic relative to the subject. In other aspects, the cells in the composition are HLA matched with the subject.

In still a further embodiment, there is provided a method of culturing a pluripotent cell comprising obtaining a frozen composition according to any of the embodiments and aspects described herein, thawing the composition and isolating a pluripotent cell therefrom, and culturing the pluripotent cell under conditions that maintain pluripotency.

Yet a further embodiment of the invention provides a method of providing a differentiated cell comprising obtaining a frozen composition according to any of the embodiments and aspects described herein, thawing the composition and isolating a pluripotent cell therefrom, culturing the pluripotent cell under differentiation conditions to provide a differentiated cell Different umbilical cord components or processed aspects may be referred to herein as a "fiber bundle", "patch", "amnion patch", "blood vessels", "gel" or "goo". Explanations and examples of these terms are provided below.

A fiber bundle is primarily composed of several collagen fibers, along with mesenchymal stem cells and few-to-none smooth muscle cells, bound together in a cylindrical format. The majority of the fiber bundle is sourced from a portion of the umbilical cord usually referred to as the 'Wharton's Jelly' or the 'Umbilical cord tissue'. The fiber bundle has a certain thickness or diameter and length that defines the physical and tensile properties of the fiber bundle. The fiber bundle can be easily sutured or glued to the target site.

A patch is primarily composed of collagen fibers, bound together in a sheet format. The patch is defined by its length, width and the thickness, which defines the physical and tensile properties of the patch. The majority of the fiber bundle is sourced from a portion of the umbilical cord usually referred to as the 'Wharton's Jelly' or the 'Umbilical cord tissue'. Patches can be easily sutured or glued to the target site. The patch is a rich source of MSCs as well.

An amnion patch is primarily composed of the epithelial membrane and its constituents. The amnion patch might or might not have collagen fibers from the portion of the umbilical cord usually referred to as Wharton's jelly.

Blood vessels can refer to the umbilical vein or the umbilical arteries. The blood vessels are primarily composed of smooth muscle cells and connective tissue, but can also carry certain or all components of Wharton's Jelly or umbilical cord tissue. Blood vessels are not a significant source of mesenchymal stem cells (unlike other products described here).

Gel or goo refers to Wharton's Jelly or umbilical cord tissue material in shredded, broken or digested form such that it forms a gelatinous consistency. Gel can be delivered to the target site by injection.

Any embodiment discussed with respect to one aspect of the invention applies to other aspects of the invention as well.

The embodiments in the Example section are understood to be embodiments of the invention that are applicable to all aspects of the invention.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

These and other objects, features, and advantages of the invention will become apparent from the detailed description below and the accompanying drawings.

FIG. 9 includes photographs of another embodiment of a patch harvester device in the vertical sliding mode.

FIG. 16 shows photographs showing migrated and confluent MSCs from WJ patch.

FIG. 20 illustrates graphs showing WJ Patch compliance over various pressures

DETAILED DESCRIPTION OF THE INVENTION

Exemplary embodiments include devices and methods for extraction and processing of *substantia gelatinea funiculi umbilicalis* (Wharton's Jelly) from an umbilical cord. In certain embodiments, a blood vessel harvester can help in removing an umbilical vein from an umbilical cord prior to harvesting a patch from the umbilical cord. In particular embodiments, a blood vessel harvester may comprise a tapered rod or dilator that runs through the blood vessel lumen and a blade that cuts off the excess umbilical cord tissue external to the blood vessel walls.

Figure 1:
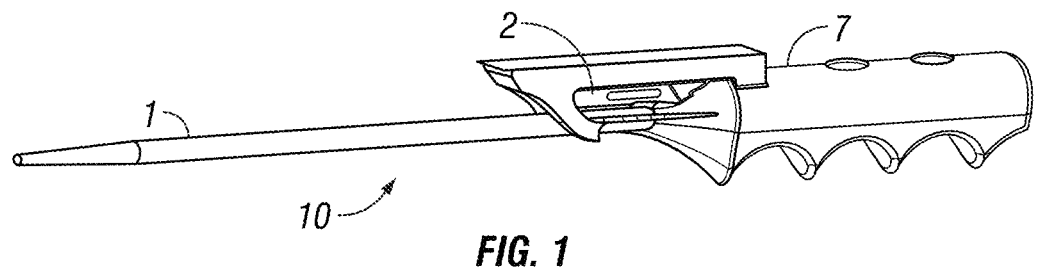
FIG. 1 is a perspective of a first embodiment of an apparatus for harvesting veins.
Figure 2:
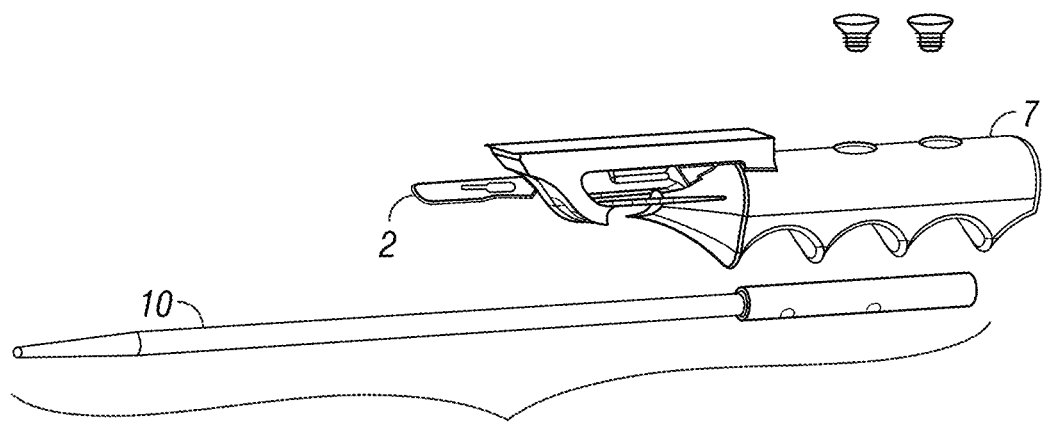
FIG. 2 is an exploded view of the embodiment of FIG. 1.
Figure 3:
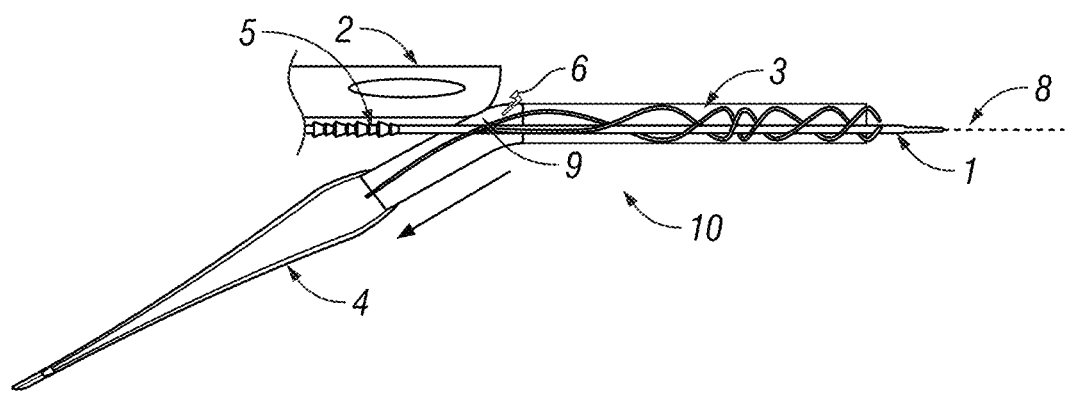
FIG. 3 is view of the embodiment of FIG. 1 during use.

FIGS. 1-2 illustrate assembled and exploded views of one such blood vessel harvester device 10. FIG. 3 illustrates a view of device 10 during use. Device 10 includes a dilator or tapered rod 1 and a blade 2 coupled to a handle 7. The blade used in certain embodiments can be a surgically sharp and disposable blade, which is coupled to the device a certain distance from the tapered rod. This distance between tapered rod 1 and the edge of the blade 2 would be greater than the typical thickness of the blood vessel wall. The handle 7 may comprise a socket for a rod attachment, hand grip, and an adapter to hold a blade and guides. The rod can be fixed to the handle using fasteners, compression fittings or clamps. In exemplary embodiments, there is a certain gap between the sharp edge of the surgical blade and the rod. In exemplary embodiments, this gap can vary from 0.05 mm to 5.0 mm. The blade could be surgical or scalpel blade; could be made out of metal, plastic or ceramic. The guides help unwind the umbilical cord for maximum efficiency in vein separation. In certain embodiments, the guides can have a narrow slit to allow the blade installation.

The vein harvester comprises a rod that passes through the lumen of the umbilical vein during us. In certain embodiments, the rod can be tapered near the end for easy of sliding of umbilical cord onto the rod. In addition, the rod can be tapered near the blade edge to force stretch the vein radially in some embodiments. The rod may also comprise sections towards the rear end to help attach the rod to the remaining components of the vein harvester. In exemplary embodiments, the rod could be make out of metal, plastic, or ceramic and could have a smooth surface for ease of sliding of the umbilical cord.

As shown in FIG. 3, the cutting line of blade 2 is aligned with a primary axis 8 of rod 1 (i.e. an axis concentric and parallel with rod 1), with a radial space 9 between cutting edge 6 and rod 1. A properly prepared umbilical cord 3 is mounted by inserting rod 1 into the lumen of umbilical vein 5 of umbilical cord 3. Once the proximal end of umbilical cord 3 is mounted, a portion of umbilical cord 3 other than umbilical vein 5 is grabbed by a hemostat or forceps 4 and pulled further down rod 1 towards blade 2, until blade 2 engages with the outer surface of umbilical cord 3.

At this stage in the harvesting process, a longitudinal slit can be cut on one side of umbilical cord 3. Radial space 9 between cutting edge 6 of blade 2 and the surface of rod 1 prevents umbilical vein 5 from being cut. As the operator pulls on umbilical cord 3, a portion of umbilical vein 5 separates from the other components of umbilical cord 3 (including most of the Wharton's Jelly and umbilical arteries). When the umbilical cord 3 has been fully pulled through, the final result would be a compressed umbilical vein 5 remaining on 1 rod a primarily intact, "butterflied" (e.g. cut along its length) umbilical cord 3.

Figure 4:
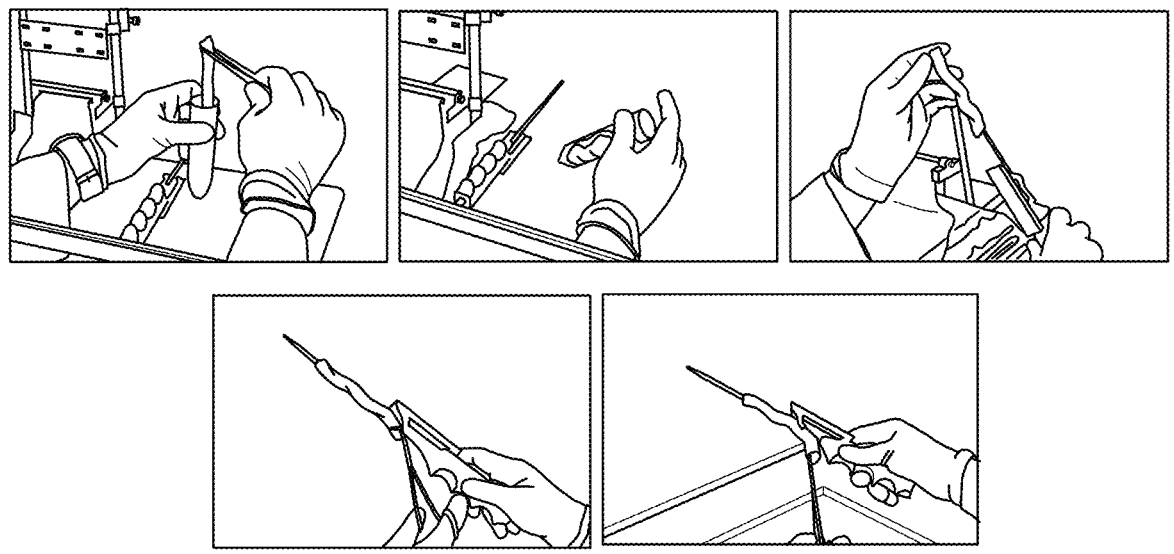
FIG. 4 are photographs showing the vein harvesting process.
Figure 5:
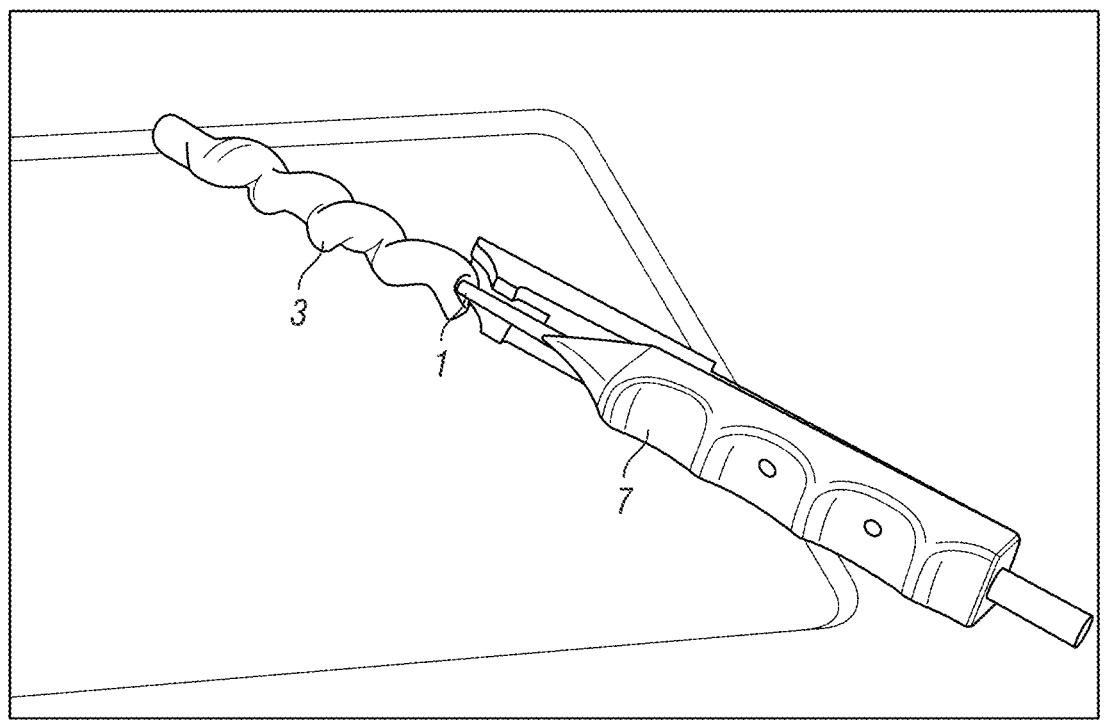
FIG. 5 is a photograph of an umbilical cord loaded on a vein harvester with the rod passing through the lumen of the umbilical vein.
Figure 6:
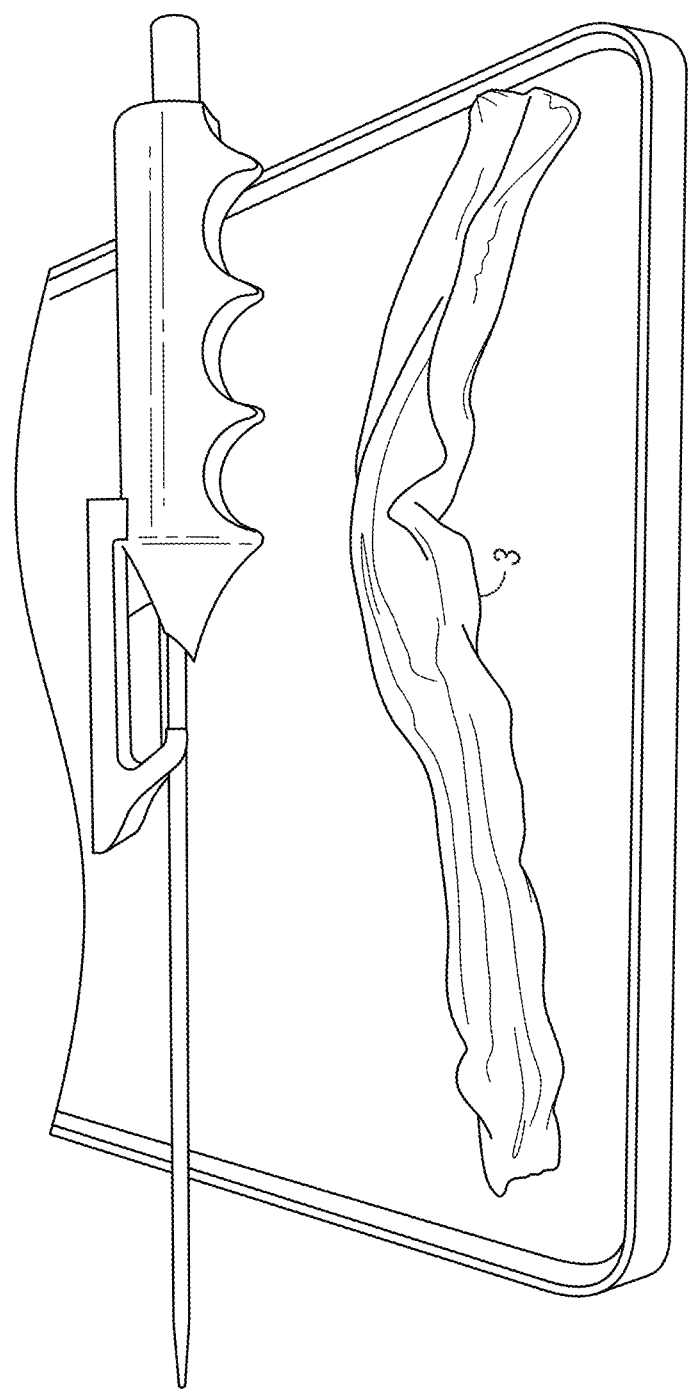
FIG. 6 is a photograph of umbilical cord after the vein separation and the vein compressed next to the blade on the harvester.

As illustrated in FIGS. 4-6, umbilical vein removal can be accomplished with the use of a device 10 comprising handle 7 with fixed tapered rod 1 and fixed blade 2.

In certain embodiments, the umbilical cord is washed in a buffered wash solution containing antibiotic like gentamycin. The washed umbilical cord can then be loaded on the vein harvester such that the rod of the vein harvester passes through the lumen of the vein. An incision can be made at the leading edge of the umbilical cord by pulling the cord end under the blade. The umbilical cord is grabbed from the sides and pulled away from the blade to start the vein-cord separation. Once the leading edge has the cord separated from the vein, the leading edge is pulled away from the blade and along the rod till the entire vein is separated from the umbilical cord.

Figure 7:
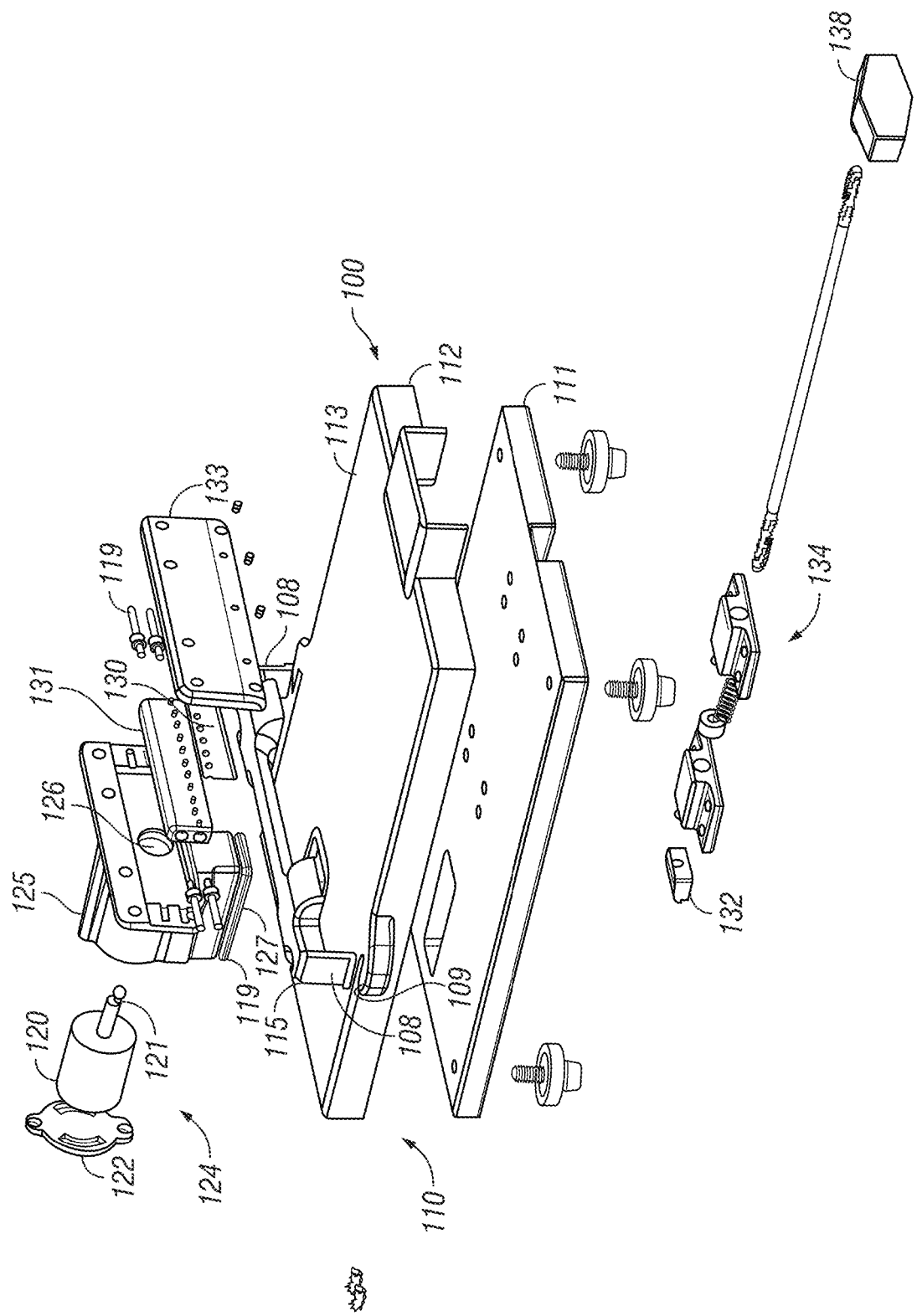
FIG. 7 is an exploded view of one embodiment of a patch harvester device.
Figure 8A:
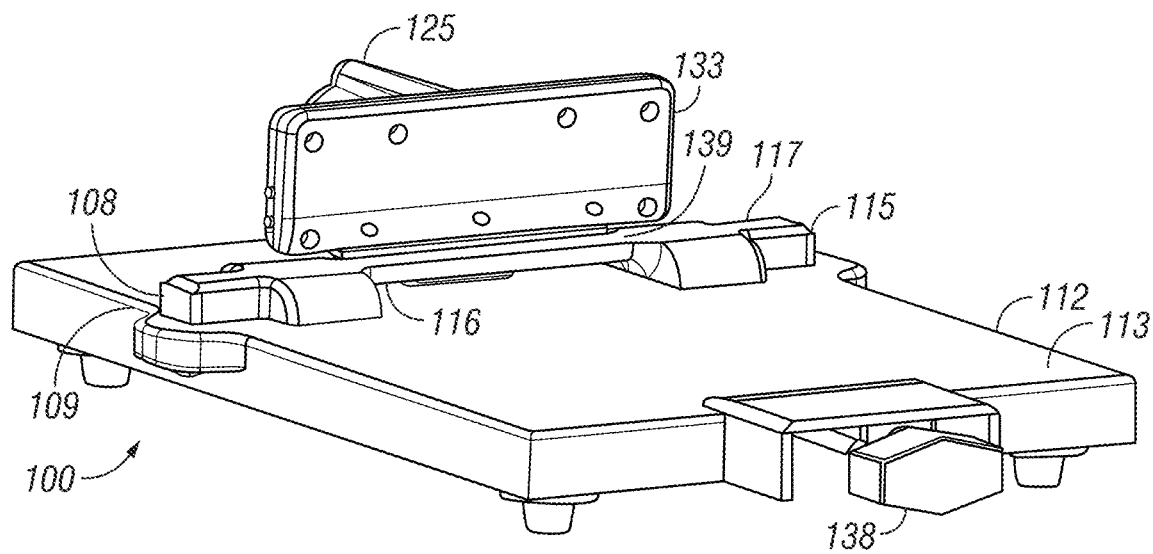
FIG. 8A-8C are different views of the embodiment of FIG. 7.
Figure 8B:
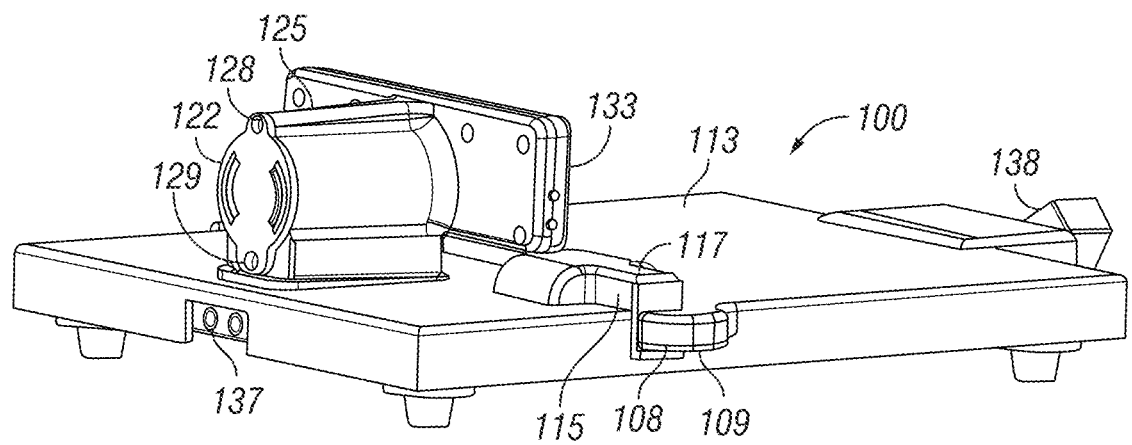
Figure 8C:
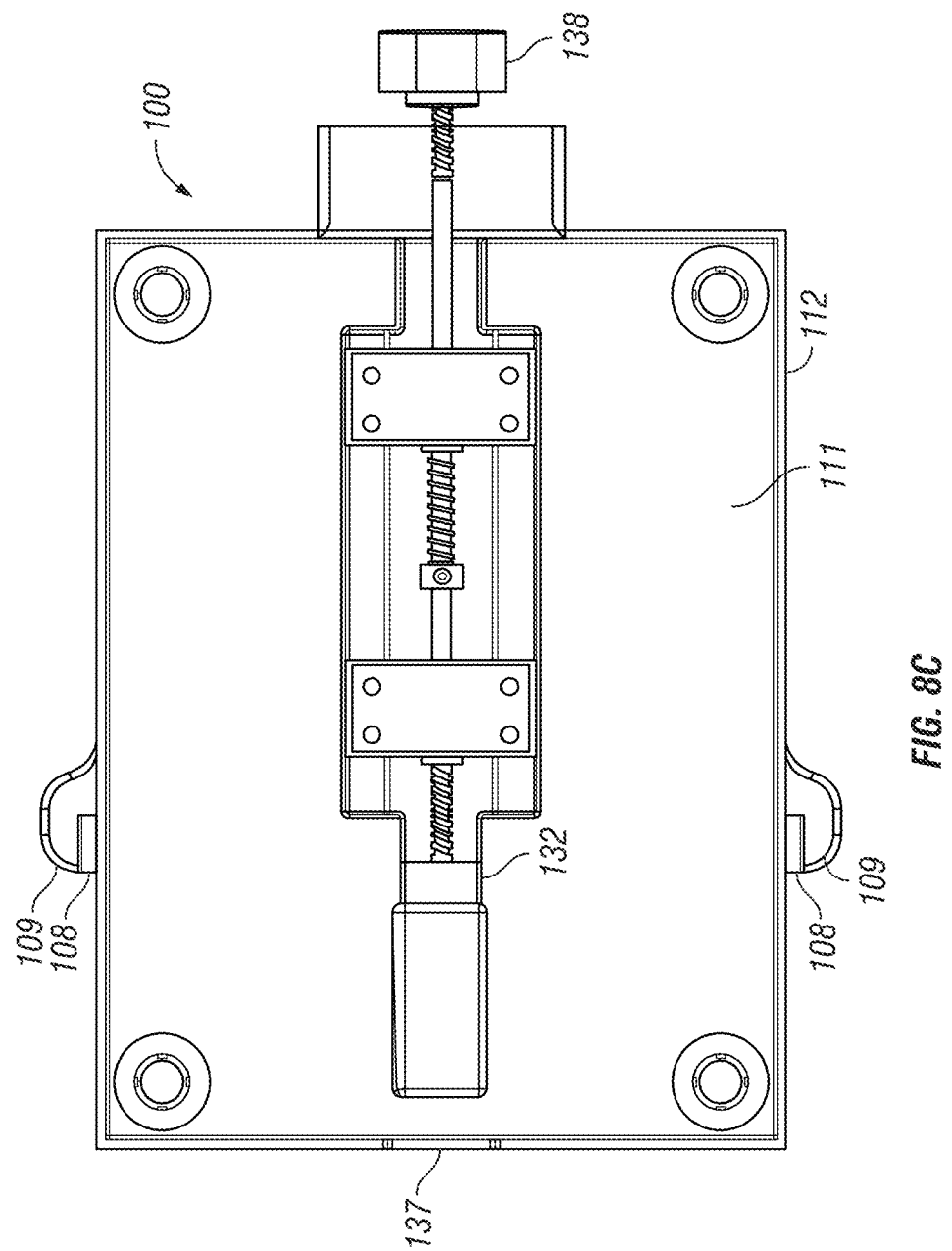

Referring now to FIGS. 7, 8A and 8B, different views of one embodiment of a patch harvester apparatus 100 for processing an umbilical cord are shown. The role of the patch harvester is to obtain a WJ patch free of any artery or amnion. In the illustrated embodiment, apparatus 100 comprises a base plate assembly 110 (comprising a base plate 111 and a cover plate 112) and a bar 115 coupled to base plate assembly 110. Apparatus 100 further comprises a motor 120 (with an eccentric pinion 121) coupled to base plate assembly 110 and a reciprocating blade 130 coupled to motor 120. In this embodiment, reciprocating blade 130 is coupled to motor 120 via a blade carrier 131 and a motor housing 125. In certain embodiments, base plate 111, cover plate 112, bar 115, blade carrier 131, reciprocating blade 130 and motor housing 125 may be disposable.

In the illustrated embodiment, motor housing 125 comprises a circular opening 126 for receiving eccentric pinion 121, which further engages a slot (not visible in the figures) on the back side of blade carrier 131. In the embodiment shown, eccentric pinion 121 drives the blade carrier 131 and reciprocating blade 130 in a reciprocating linear motion. In the embodiment shown, motor cover 122 holds electric motor 125 in place and provides for electrical terminals 128 and 129 to be connected to external power supply. In certain embodiments, other mechanisms can be incorporated to provide reciprocal actuation of the blade. Such mechanisms include for example, a pivot motor or pneumatic cylinders.

Bar 115 is spaced from a planar surface 113 of base plate assembly 110 such that a gap 116 exists between bar 115 planar surface 113 and bar 115. As explained further below, during operation of apparatus 100, an umbilical cord can be directed through gap 116 and wrapped around bar 115. Gap 116 can be sized to provide frictional resistance as the umbilical cord is pulled away from bar 115 during patch harvesting.

During operation of apparatus 100, blade carrier 131 is constrained to move in the same plane as that of reciprocating blade 130 based on the sliding shafts 119 located between motor housing 125 and a blade cover 133. Reciprocating blade 130 can be coupled to blade carrier 131 and is covered by blade cover 133, which is further coupled to motor housing 125. In certain embodiments, reciprocating blade 130 can be further pinned down against blade carrier 131 using spring plungers or compression fitting. In this embodiment, motor 120 is held in place in motor housing 125 via a motor cover 122 that couples to the backside of motor housing.

In the embodiment shown, motor housing 125 is coupled to base plate 111 using spring plungers 137 and 132 from two opposite ends that engage grooves 127 on the bottom of motor housing 125. Plunger 132 is part of a pull release mechanism 134 that locks motor housing 125 when pushed into base plate 111. Pull release mechanism 134 comprises a handle 138, which can be pulled to release a motor and blade assembly 124 (comprising motor 120, motor housing 125, blade 130, blade carrier 131, blade cover 133 and related components) from base plate assembly 110. In this manner, motor and blade assembly 124 can be quickly and easily coupled and de-coupled from base plate assembly 110.

In this embodiment, bar 115 locks into the cover plate 112 via prongs 108 at each end that engage designated grooves 109 in cover plate 112. Bar 115 comprises a flat side 117 that is proximal to reciprocating blade 130. Apparatus 100 is configured such that a gap 139 exists between flat side 117 and a cutting edge 135 of blade 130. Gap 139 determines the thickness of a WJ patch obtained from an umbilical cord during operation of apparatus 100. Gap 139 can be easily modified, for example, by using a different bar 115 with slight variations in its dimensions. In certain embodiments, apparatus 100 may include multiple bars with different dimensions so that a user can set gap 139 at a particular dimension to obtain the desired thickness of the WJ patch. In other variations, motor housing or blade orientation angle can be changed to change the gap 139.

Figure 10:
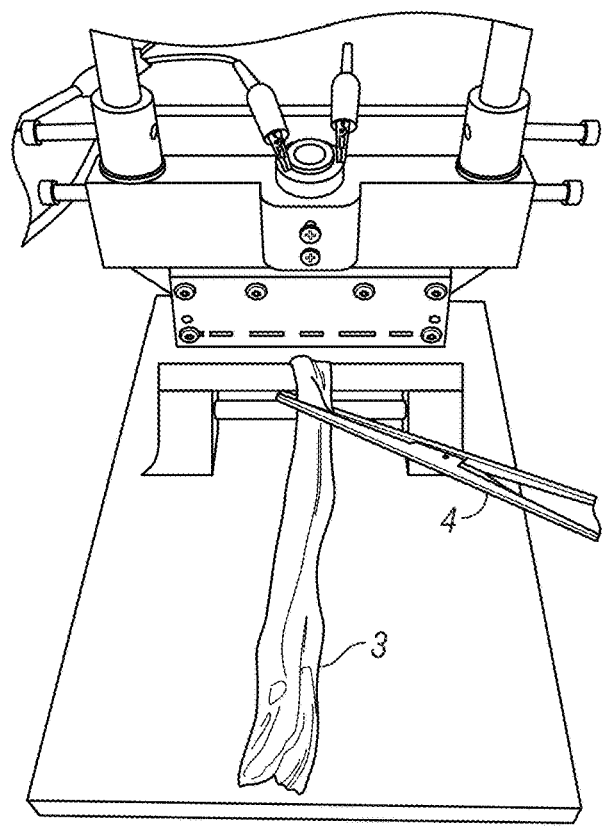
FIG. 10 is a 3D printed version of a patch harvester device in the vertical sliding mode.

In exemplary embodiments, apparatus 100 can be operated in the following manner to harvest a patch from an umbilical cord. Initially, apparatus 100 can be partially assembled such that motor and blade assembly 124 is not coupled to base plate assembly 110. After running an umbilical cord through a vein harvester (e.g. vein harvester 10 shown and described in FIGS. 1-3), one end of the umbilical cord is directed between bar 115 and cover plate 112 and wrapped over bar 115. The umbilical cord is wrapped around the bar 115 such that the amnion is facing outwards. An example of the placement of umbilical cord 3 is shown in FIG. 10.

After the umbilical cord has been wrapped around bar 115, motor and blade assembly 124 is coupled to base plate assembly 110. Cutting edge 135 of blade 130 can then make the initial cut into the umbilical cord, which marks the start of the patch. The top free end of the umbilical cord is grabbed using forceps or serrated tweezer 4, as shown in FIG. 10. With the cutting edge 135 set at the desired distance from bar 115, motor 120 can then be switched on. The range of distance 139 can be anywhere between 0.1 mm up to a few millimeters. The first end of the umbilical cord is then pulled with the tweezers away from bar 115 and blade 130 (e.g. towards the other free end of the umbilical cord) to start the patch extraction. The amnion, along with the two arteries and remnant Wharton's Jelly is separated from the WJ Patch. The Wharton's Jelly patch remains attached to the umbilical cord stub held by the tweezer. The amnion along with arteries and excess WJ is collected behind blade 130 and can be retrieved after the cord has been processed. The WJ patch can be separated from the umbilical cord stub using a surgical blade.

Referring now to FIG. 9, photographs of an alternate embodiment of a patch harvester apparatus are shown. This embodiment operates in a manner similar to previously-described apparatus 100. However, this embodiment includes adjustment mechanisms that allow the bar (around which the umbilical cord is wrapped) to move in the X-Y plane and the motor and blade assembly to move in the Z-plane perpendicular to the bar adjustment plane.

In this embodiment, the gap between the cutting bar and the blade can be set to a specified distance or it can be varied by sliding the motor and blade assembly to move in the Y-plane. The sliding mode of the motor and blade assembly allows to move the motor assembly away from the cutting bar, which also allows for loading and unloading of the umbilical cord without fully separating the motor and blade assembly from the base plate.

FIG. 10 illustrates an embodiment of a patch harvester apparatus for processing an umbilical cord in which components are manufactured by a three-dimensional (3D) printing process. In this embodiment, umbilical cord 3 is being pulled with forceps 4 after umbilical cord 3 has been wrapped around the cutting bar.

Figure 11:
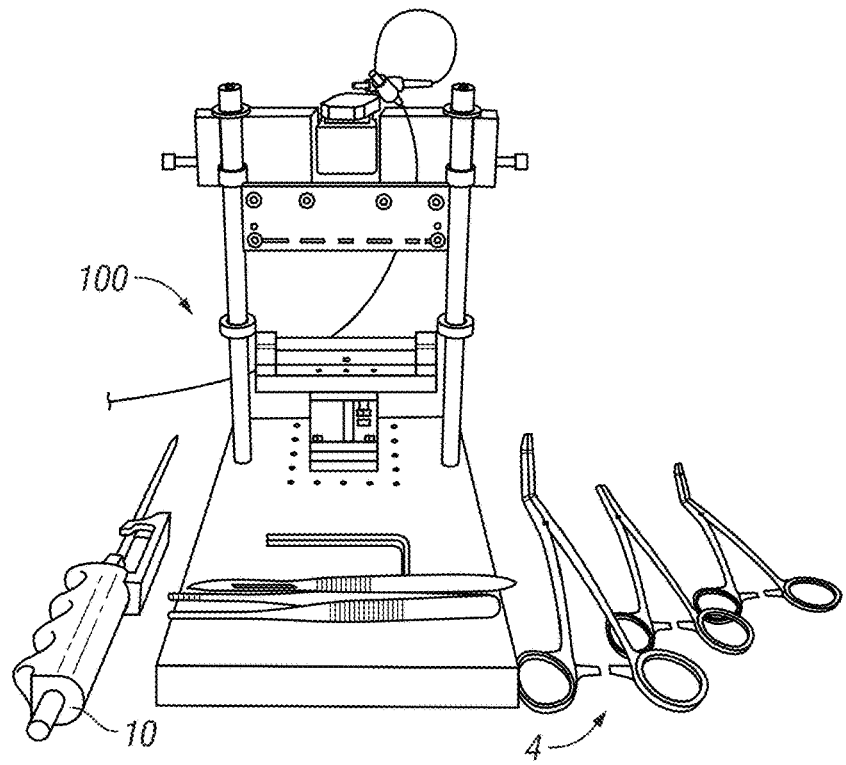
FIG. 11 is a photograph of a complete WJ Patch extraction system.

FIG. 11 illustrates an embodiment of a kit or system WJ patch extraction. This embodiment includes a vein harvester 10, a patch harvester apparatus 100, and serrated tweezers or forceps 4 to grasp the umbilical cord during patch harvesting.

Figure 12:
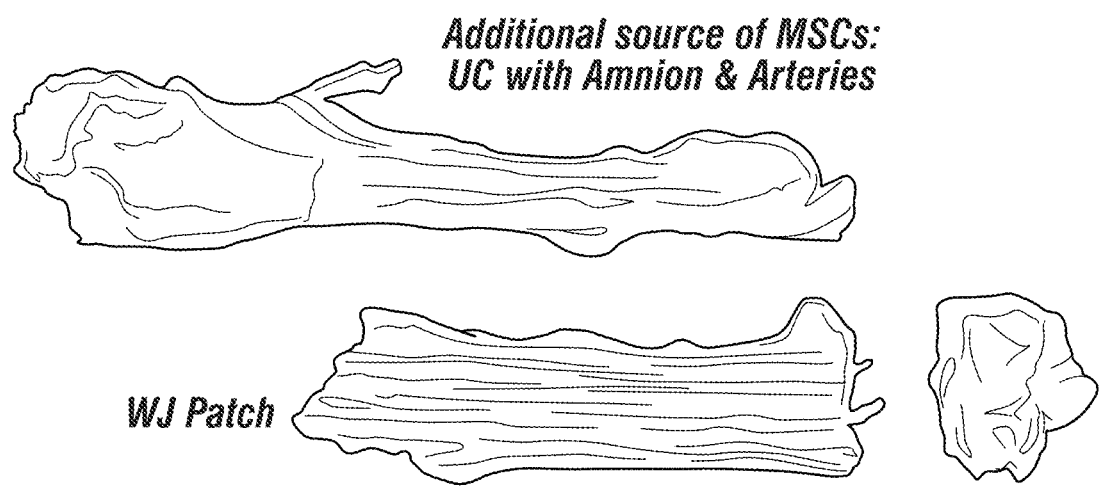
FIG. 12 is a photograph showing the WJ Patch, UC Stub—where the serrated tweezers hold the UC, leftover UC with amnion, arteries and excess WJ.

FIG. 12 is a photograph of a WJ patch harvested using the apparatus and methods described herein. In addition, a photograph of the umbilical stub (e.g. the portion where the serrated tweezers grasp during patch harvesting) is shown, along with the leftover portion of the umbilical cord with amnion, arteries and excess WJ. As compared to previously used apparatus and methods, the WJ patch harvested according to embodiments of the present disclosure include a more uniform thickness and fewer voids (e.g. holes).

Figure 13:
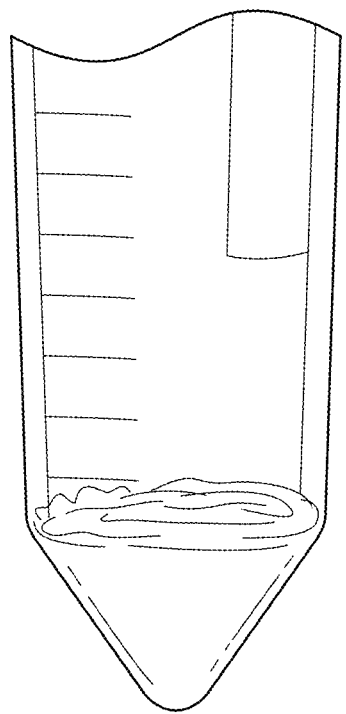
FIG. 13 is a photograph of a WJ Patch homogenized to a gel like consistency.
Figure 14:
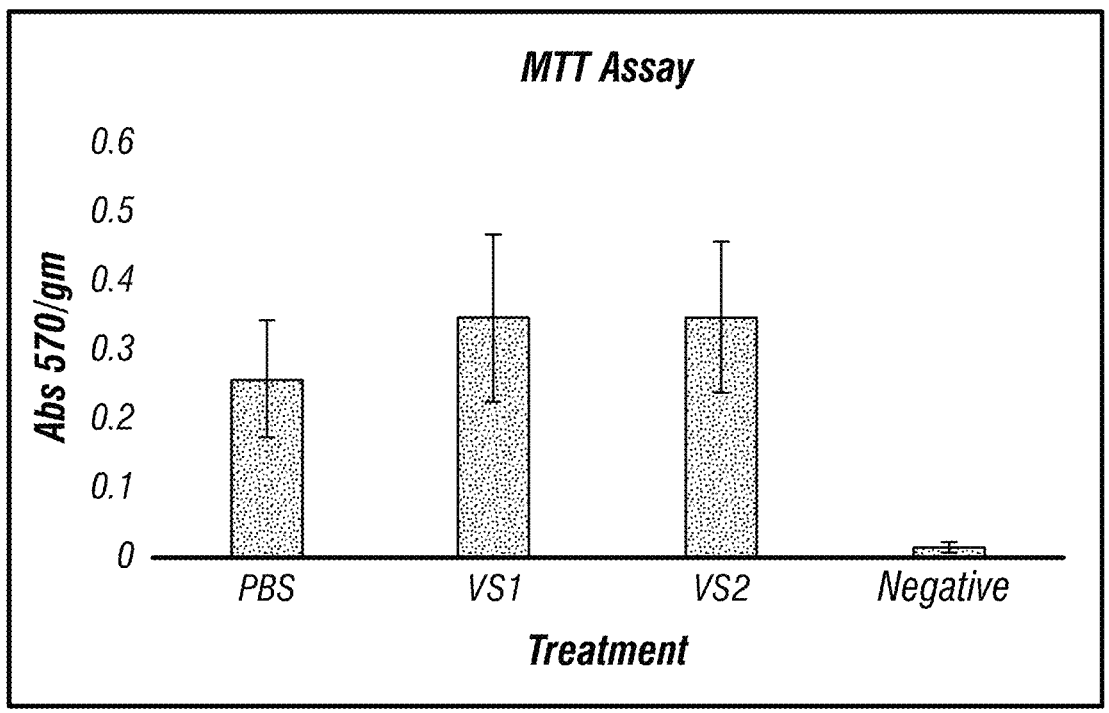
FIG. 14 is a graph that shows cells to be alive in a WJ gel (PBS) obtained by homogenization of the WJ Patch.

Referring now to FIG. 13, the harvested WJ patch can be homogenized to a gel like consistency using a homogenizer to create a WJ gel (or "goo"). An example of such a WJ gel is shown in the FIG. 13. Even after homogenization, the cells in the WJ gel were found to be viable as measured using the MTT assay as shown in FIG. 14. In FIG. 14, the cells were also found to be alive post cryopreservation treatment (VS1 and VS2). Negative represents the control obtained by plunging cells into liquid nitrogen without any cryoprotectant.

Figure 15:
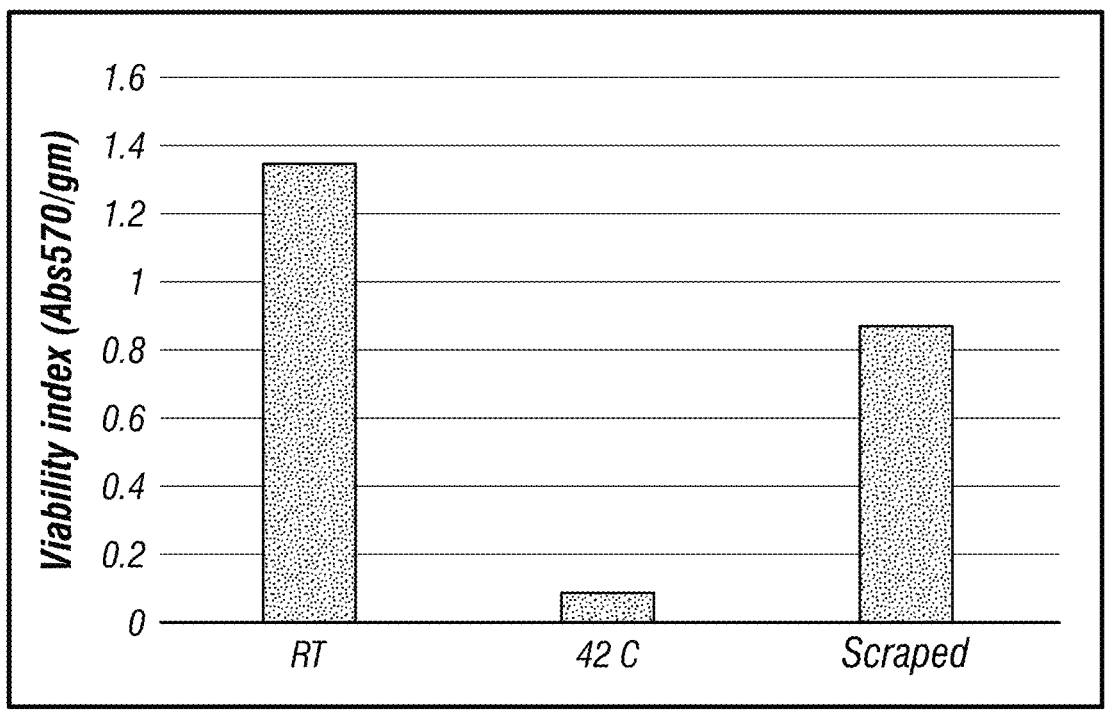
FIG. 15 is a graph showing both WJ patch and scraped WJ yields viable cells.

Referring now to FIG. 15, a graph shows both WJ patch and scraped WJ yields viable cells. Also shown in FIG. 15, storing an umbilical cord at 42 C for over 2 hours affects the cell viability significantly. The data illustrated in FIG. 15 was obtained according to the following procedure. In order to ensure that the harvested WJ patch included live cells, a WJ Patch was obtained from an umbilical cord according the methods and apparatus described herein. An MTT Assay was performed on the patch with the patch incubated with MTT (3-(4,5-dimethylthiazol-2-yl)-2,5-diphenyltetrazolium bromide) overnight. Post incubation, the dye was extracted from the cells and tissue using a solubilization solution, comprising a surfactant dissolved in hydrochloric acid. The absorbance of this dye was measured and compared with WJ gel observed by scraping the WJ manually from the same umbilical cord. Both the WJ patch and scraped WJ was found to contain live cells post harvesting. When the umbilical cord was stored and washed in PBS solution maintained at 42 C for 2 hours, the viability of the cells was reduced significantly.

Referring now to FIG. 16, photographs illustrate migrated and confluent mesenchymal stem cells (MSCs) from a WJ patch. Wharton's Jelly is widely used as the primary source for MSCs. MSCs can be obtained from WJ Patch by cutting the WJ patch into smaller pieces and plating these pieces on a cell culture plate, ideally within 5 mm gap between adjacent pieces. Alternatively, the WJ patch or a part of it can be plated directly on a cell culture plate. Another option is plating a perforated or meshed WJ Patch directly on a cell culture plate. After plating the WJ cell source, favorable media is added to the cell culture plates and placed in the incubator. The cells migrate out of the tissue and attached themselves to plate surface immediately next to tissue.

Table 1 below shows the MSC cell count from different parts of an umbilical cord or WJ Patch when the cells reached confluency.

TABLE 1

| | Concentration (Cells/mL) | Total cell Count |
|---|---|---|
| Randomly obtained piece of WJ | 3.50E+06 | 1.05E+06 |
| WJ Patch originally facing the amnion | 1.50E+05 | 4.50E+04 |
| WJ Patch originally facing the vein | 1.41E+06 | 4.23E+05 |
| Leftover amnion with excess WJ | 2.50E+06 | 7.65E+05 |

In addition to using the harvested WJ Patch as the source of MSCs, the leftover amnion with umbilical arteries and excess WJ can also be used as a viable source of MSCs. Table 1 above shows that MSCs were obtained from the leftover portion of the umbilical cord, post WJ Patch harvesting.

Figure 17:
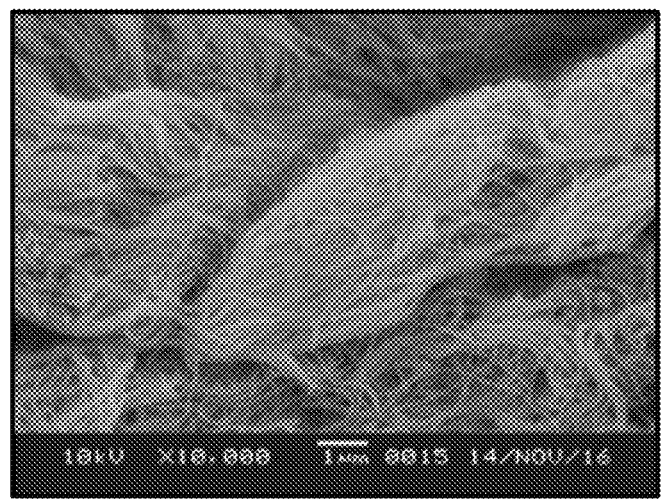
FIG. 17 shows SEM (Scanning electron microscopy) images of a WJ Patch showing aligned collagen fiber bundles.
Figure 18:
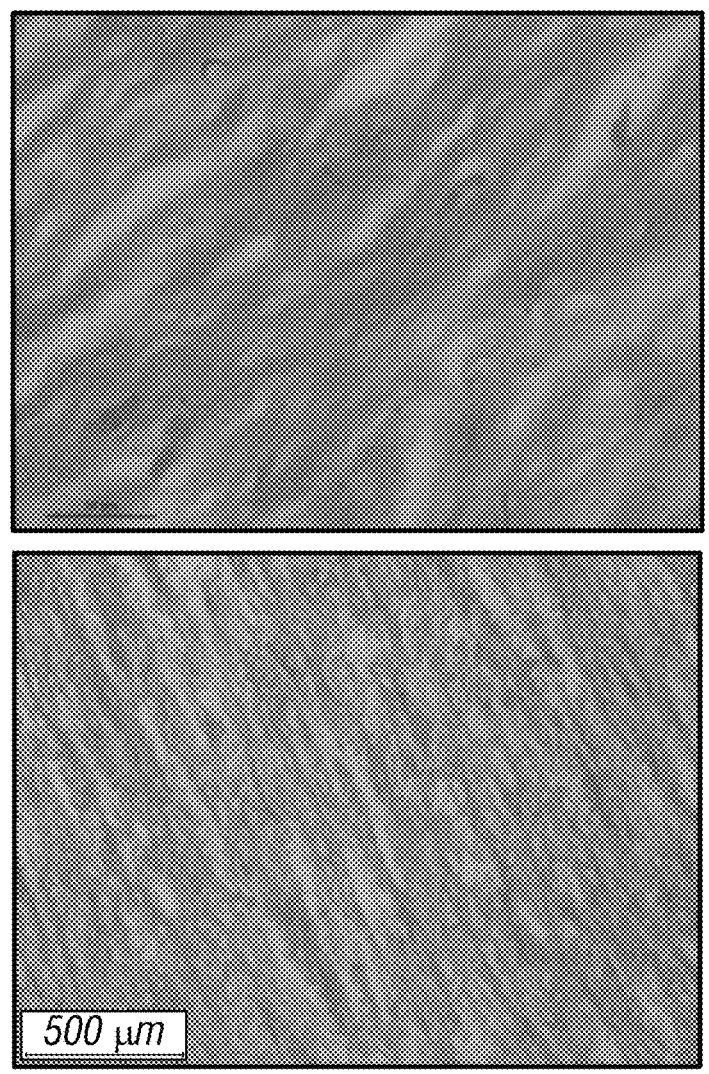
FIG. 18 shows images of trichrome stained lateral section of a WJ Patch showing blue colored collagen fibers aligned parallel.

The inventors found that collagen fiber bundles run parallel to umbilical arteries. Since umbilical arteries might be helically wrapped around the umbilical vein, the collagen fiber bundles can be helically wrapped around a vein in an intact umbilical cord. However, vein harvesting process described in this invention unwinds the umbilical arteries and therefore aligns the collagen fiber bundles along the length of the WJ Patch. This can be seen from SEM and trichrome images obtained from a WJ Patch shown in FIGS. 17 and 18.

Figure 19:
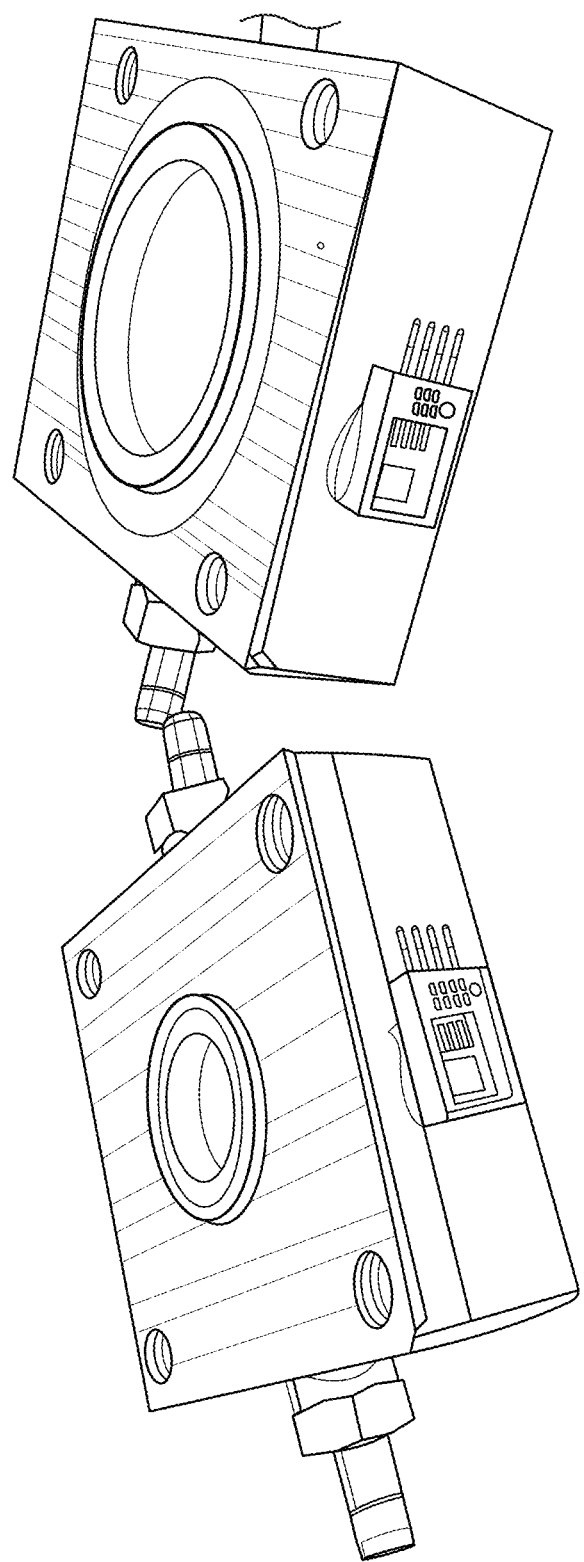
FIG. 19 is a photograph showing custom built chamber to test the compliance of a WJ Patch.

A WJ Patch is elastic, not permeable to water and can withstand relatively high pressures (in the physiological range). The inventors fabricated a compliance testing setup shown in FIG. 19 that held a WJ Patch sandwiched between two hollow chambers. The chambers were connected to an external commercial pressure sensor to measure the hydrostatic pressure inside the chamber. Both the chambers were filled with PBS. Using a syringe mounted on a syringe pump, a specified volume of water was cyclically injected into one of the chambers. The corresponding pressure was recorded. The peak to peak pressure rise were averaged and used to obtain the tissue compliance values as a function of the chamber pressures. The burst pressure for a thin WJ Patch (approximately 1 mm thickness) was over 500 mmHg. The initial leakage pressure of two WJ Patches sutured to each other was found to be 360 mmHg, with the leakage occurring at the suture line.

FIG. 20 shows WJ Patch compliance over various pressures. The compliance properties of WJ Patch are similar to that of a physiological tissue. During the testing to obtain the data in FIG. 20, the thin films were approximately 1 mm and the thick film was approximately 3 mm in thickness.

Figure 21:
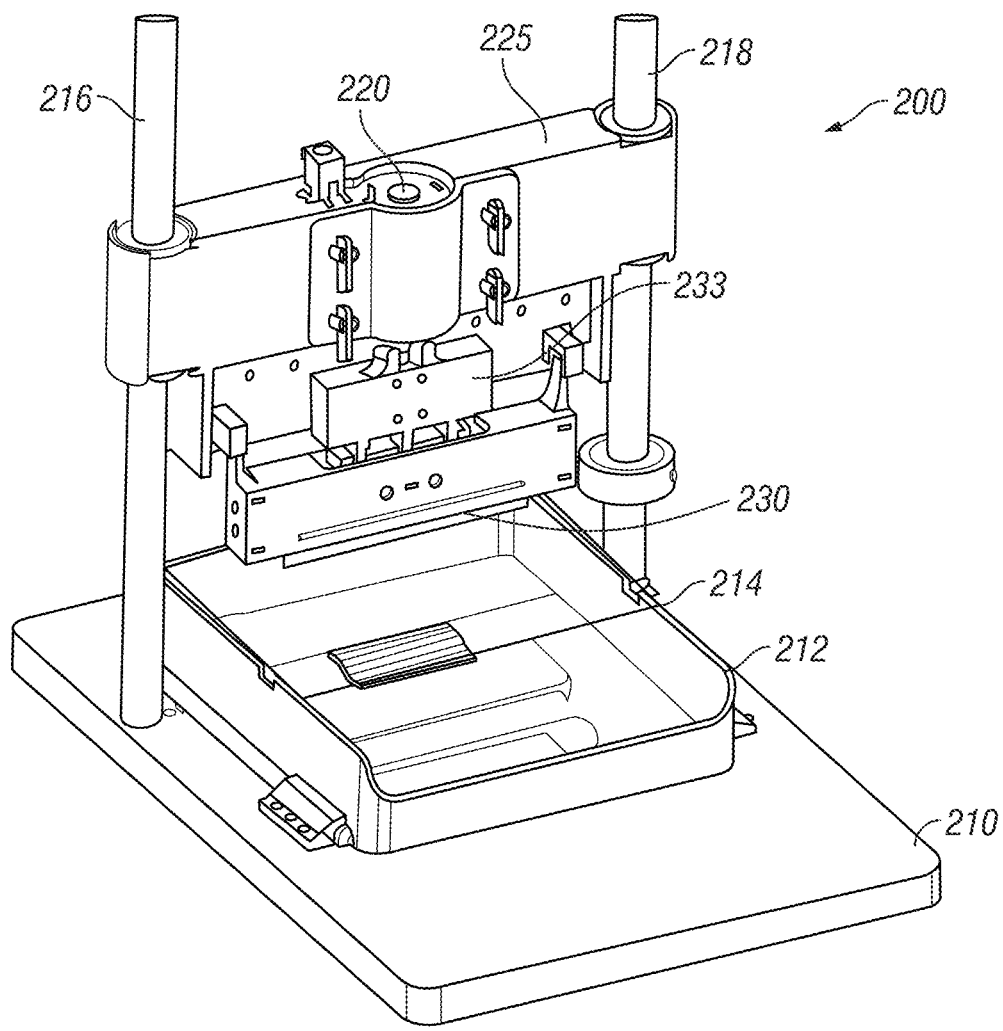
FIGS. 21-23 illustrate perspective and orthographic views of one embodiment of a patch harvester apparatus.
Figure 22:
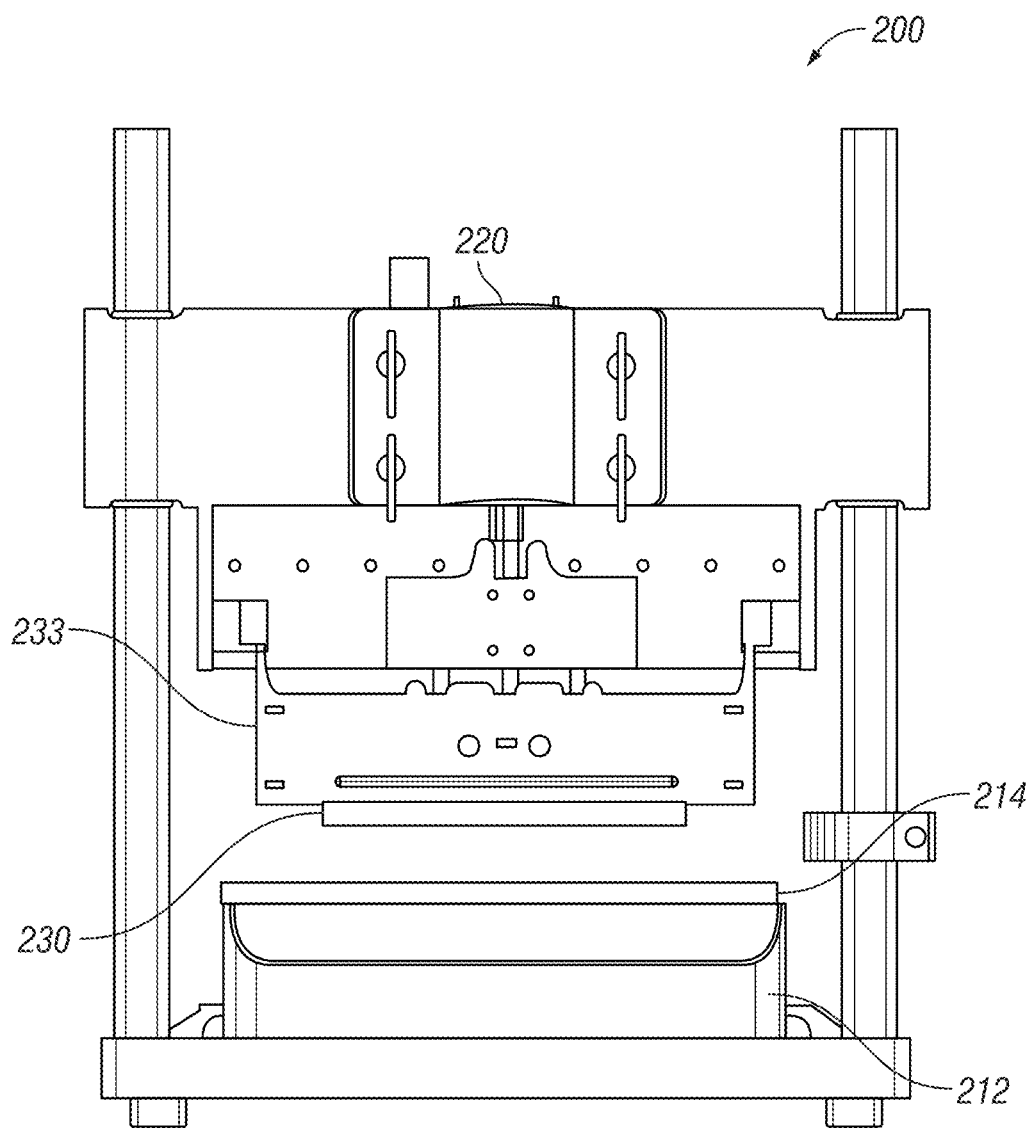
Figure 23:
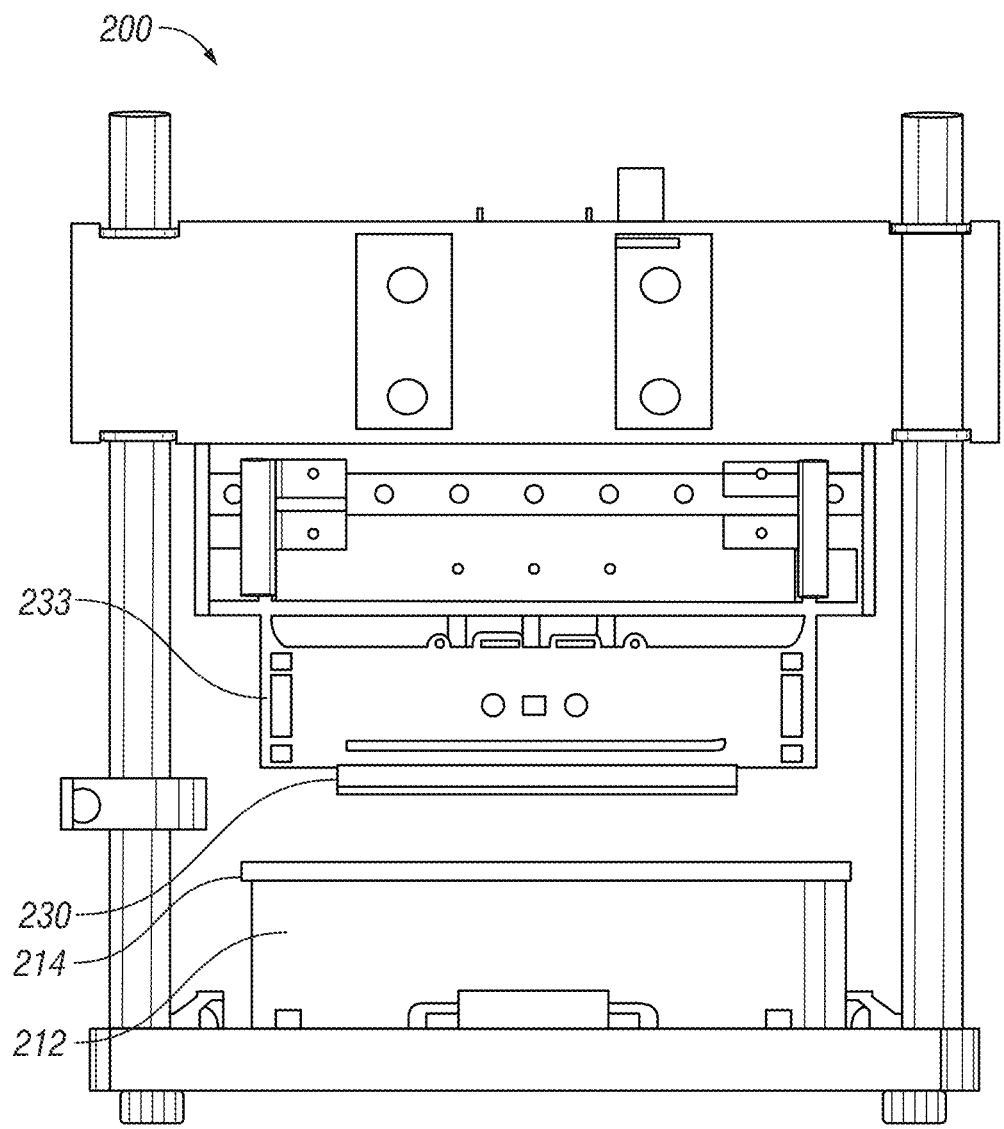

Referring now to FIGS. 21-23 a patch harvester apparatus 200 comprises features and components similar to previously described embodiments (see e.g. FIGS. 9-11), but also includes additional components not included in such embodiments. The principles of operation of patch harvester apparatus 200 are also similar to those of previously-described embodiments, in that a reciprocating blade is used to harvest a patch from an umbilical cord. In this embodiment a motor 220 is coupled to a chassis 225 and a blade housing 233 with a blade 230. Apparatus 200 also comprises a base plate 210 that supports a receptacle 212 with a lid 214. In addition, base plate 210 supports vertical members 216 and 218 that allow adjustment of chassis 225 (and associated components, including blade 230) in a direction perpendicular to lid 214.

During operation, an umbilical cord can be placed on lid 214 and blade 230 adjusted to a particular location on vertical members 216 and 218 so that the desired gap exists between blade 230 and lid 214. Similar to previous embodiments, motor 220 can then be operated to move blade 230 back and forth in a reciprocating motion and harvest a WJ patch from the umbilical cord (e.g. via an eccentric pinion 229 of motor 220 engaging a slot 228 in blade housing 233). The harvested patch can be stored in receptacle 212 until it is needed for further use.

Figure 24:
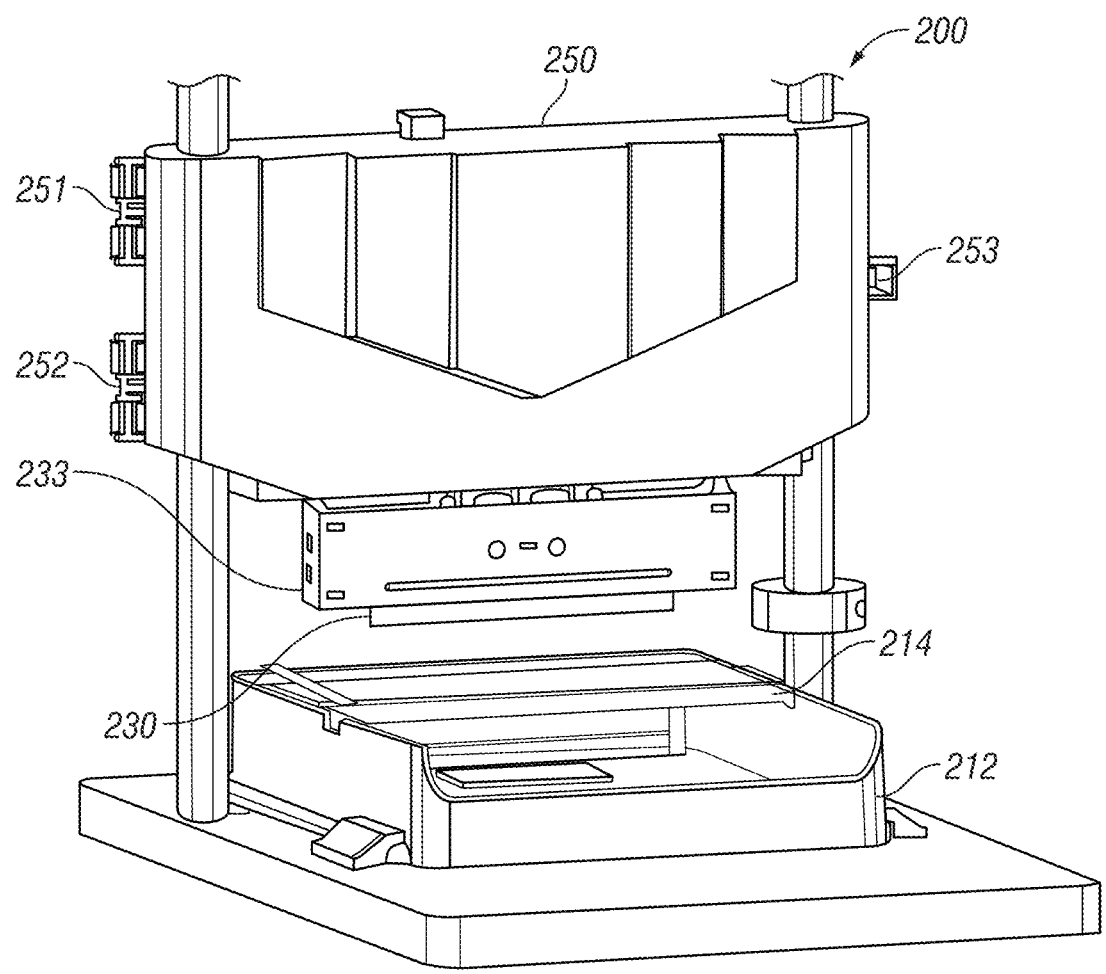
FIGS. 24-25 illustrates perspective view and orthographic views of the embodiment of FIGS. 21-23 with a chassis cover.
Figure 25:
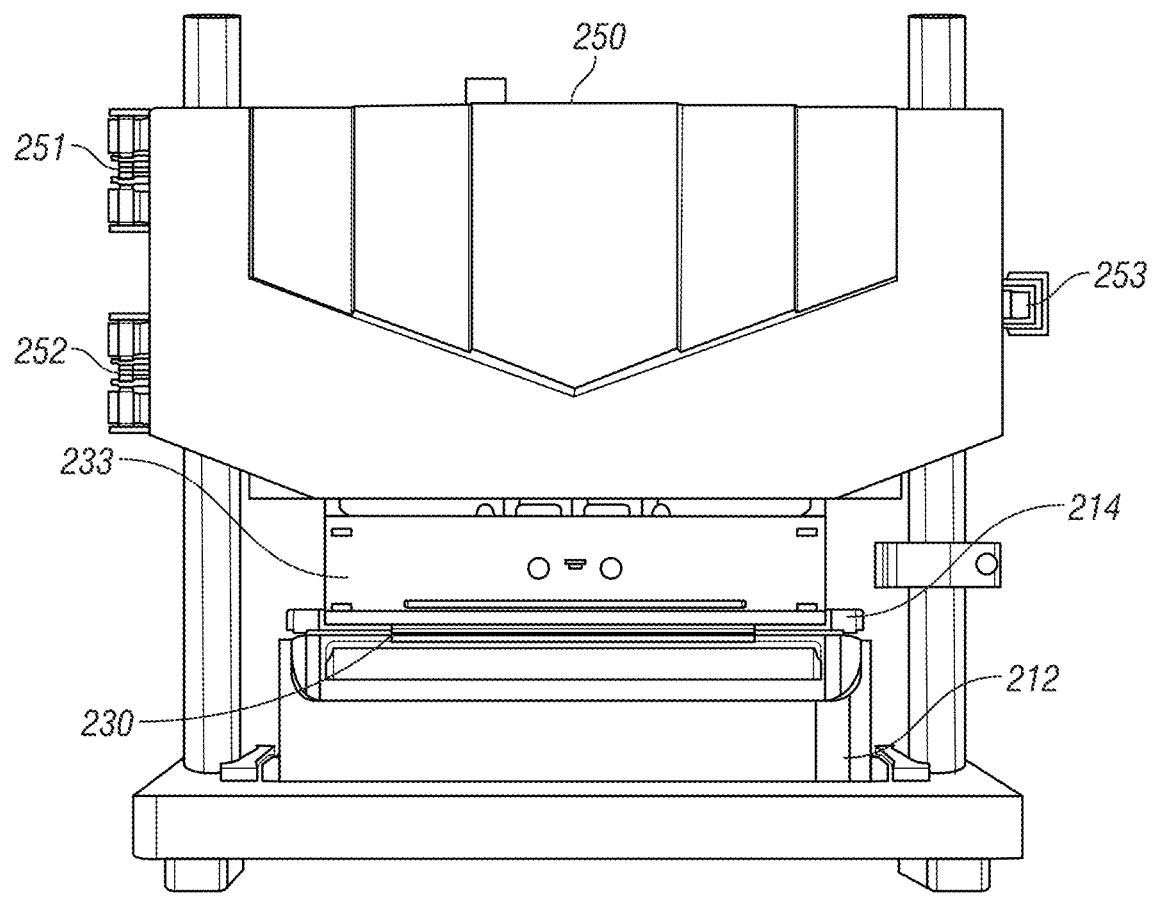
Figure 26:
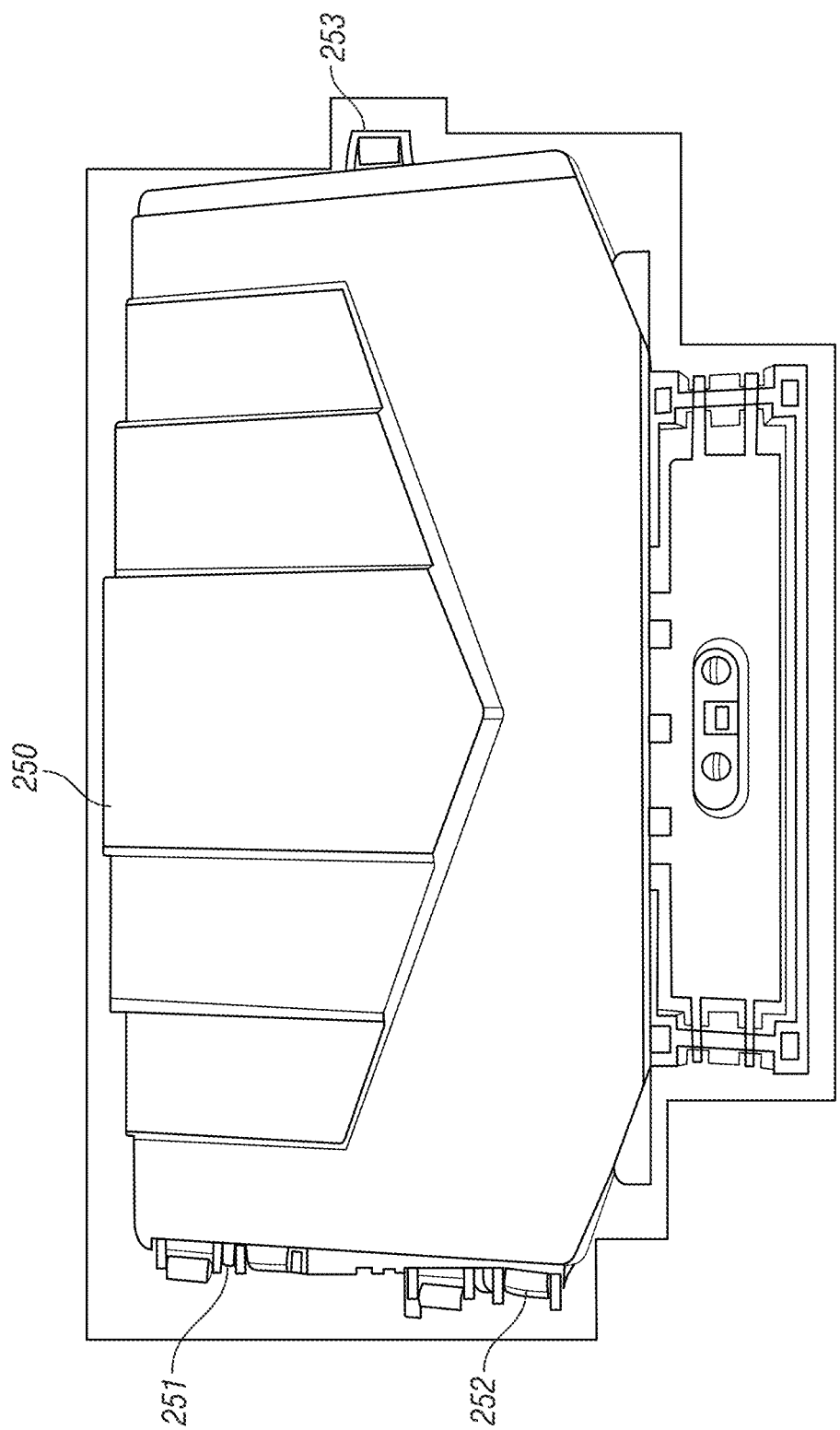
FIGS. 26-27 illustrate the chassis cover of FIG. 24 in the closed and open positions.
Figure 27:
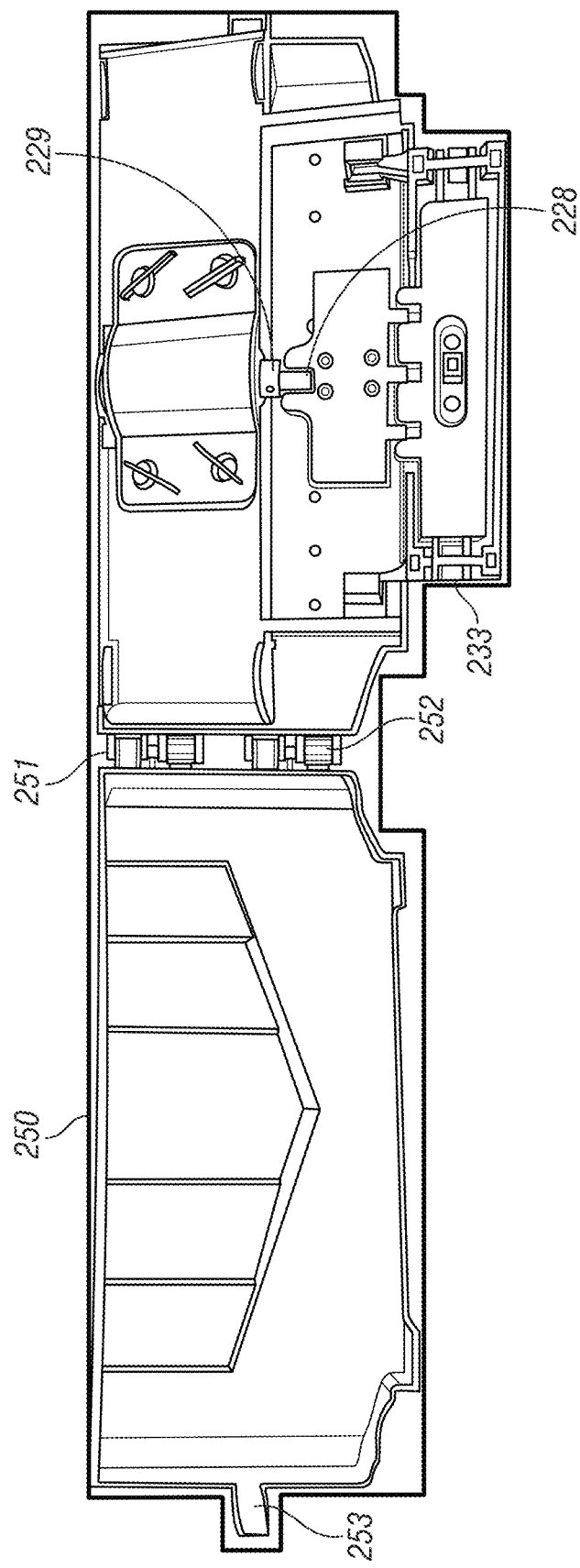

FIGS. 21-23 illustrate apparatus 200 without a cover on chassis 225 and the associated components. FIGS. 24-25 illustrate apparatus 200 with a cover 250 that is configured to cover chassis 225 and motor 220. Cover 250 includes hinges 251 and 252 as well as latching mechanism 253 (shown in FIG. 25). When latching mechanism 253 is released, cover 250 can be opened via hinges 251 and 252. FIG. 26 shows cover 250 separated from apparatus in a closed position, while FIG. 27 illustrates cover 250 in an open position.

Figure 28:
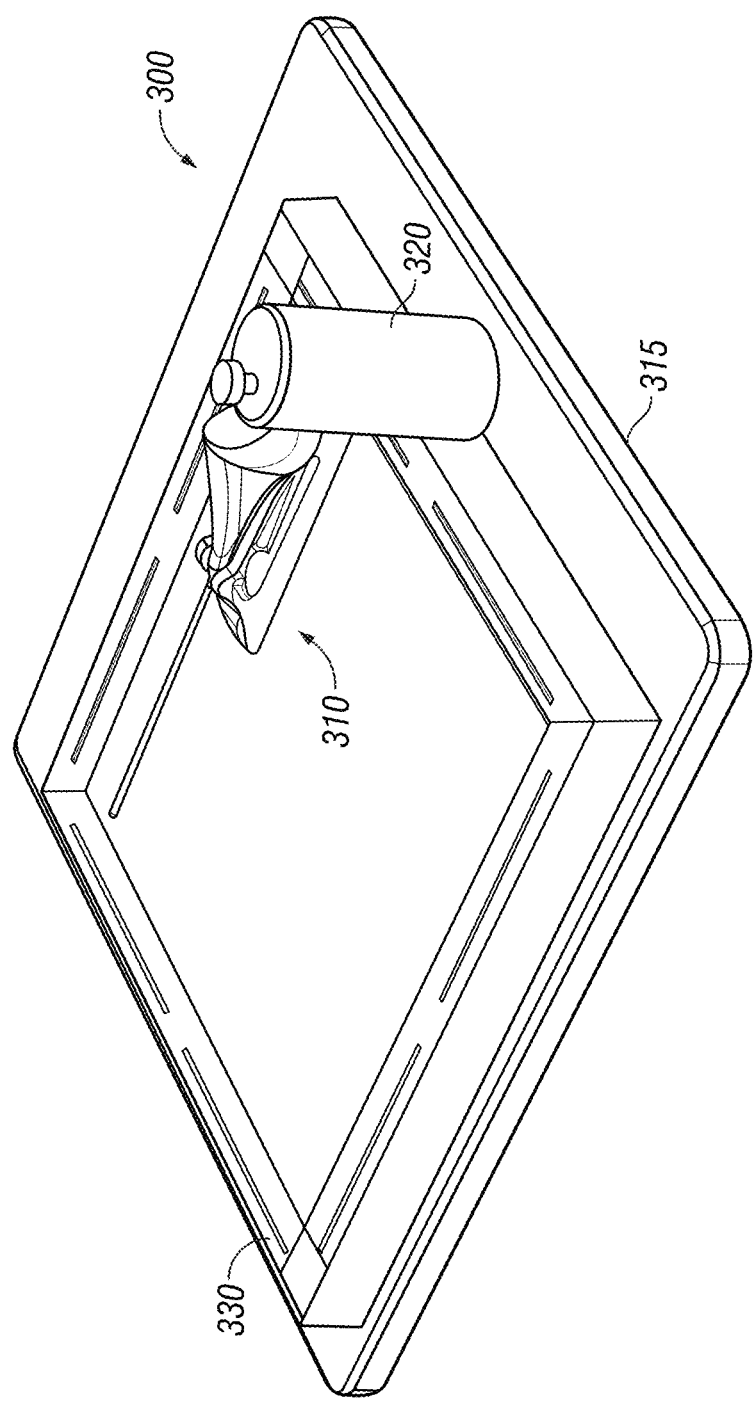
FIG. 28 illustrates a vein harvester assembly.

FIG. 28 illustrates a vein harvester assembly 300 comprising a vein harvester 310 coupled to a support member 320 that extends perpendicular from a base plate 315. Vein harvester assembly 300 further comprises a receptacle 330 that is configured to positively engage with base plate 315 in order to secure receptacle 330 to base plate 315. Vein harvester 310 can then be used in a manner (e.g. similar to that previously described for FIGS. 1-6 above) to harvest a vein from an umbilical cord.

Figure 29:
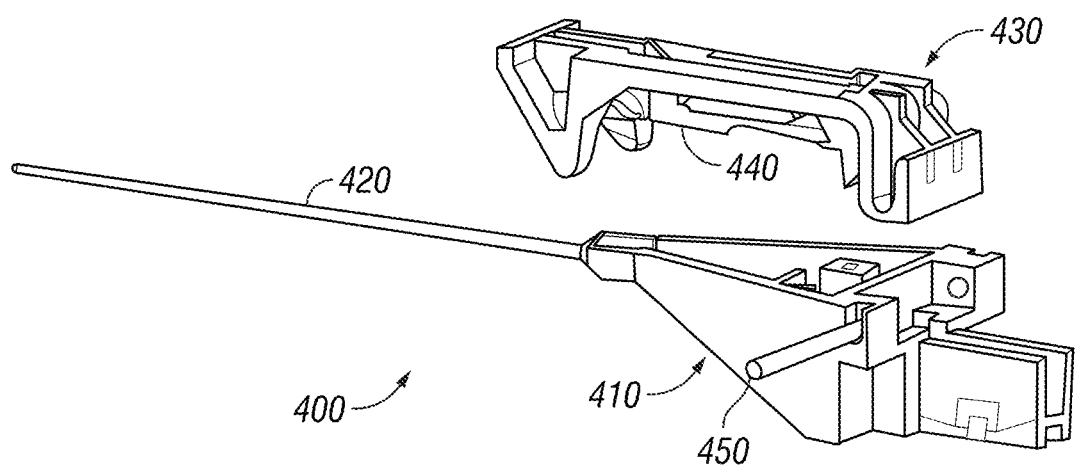
FIGS. 29-30 illustrate exploded and assembled views of a vein harvester.
Figure 30:
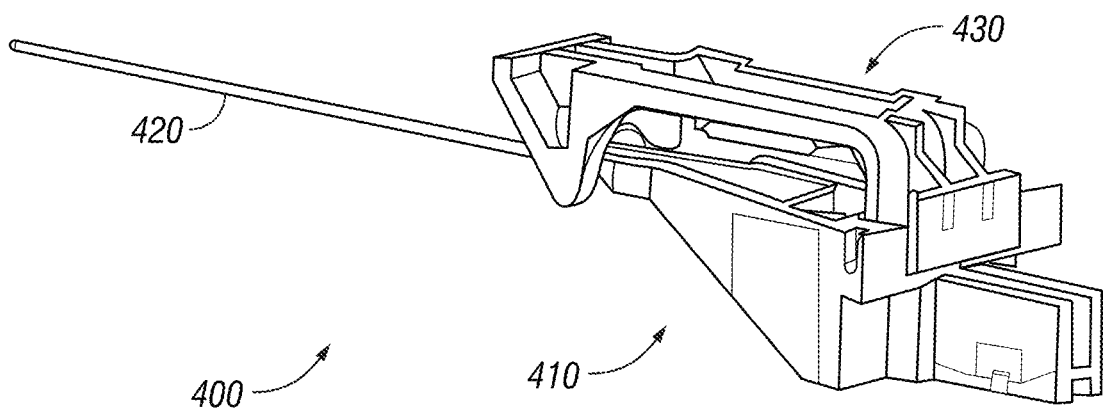

Referring now to FIGS. 29 and 30, a particular embodiment of a vein harvester 400 is shown that comprises components manufactured using injection molding. In this embodiment, vein harvester comprises a base component 410 with a rod 420, and a blade housing 430 securing a blade 440. FIG. 29 illustrates base component 410 separated from blade housing 430, while FIG. 30 illustrates base component 410 and blade housing 430 assembled. As shown in FIG. 29, a pin 450 can be used to secure blade housing 430 to base component 410. Pin 450 can also be removed from base component 410 and blade housing 430 to allow blade housing 430 to be separated from base component 410.

Figure 31:
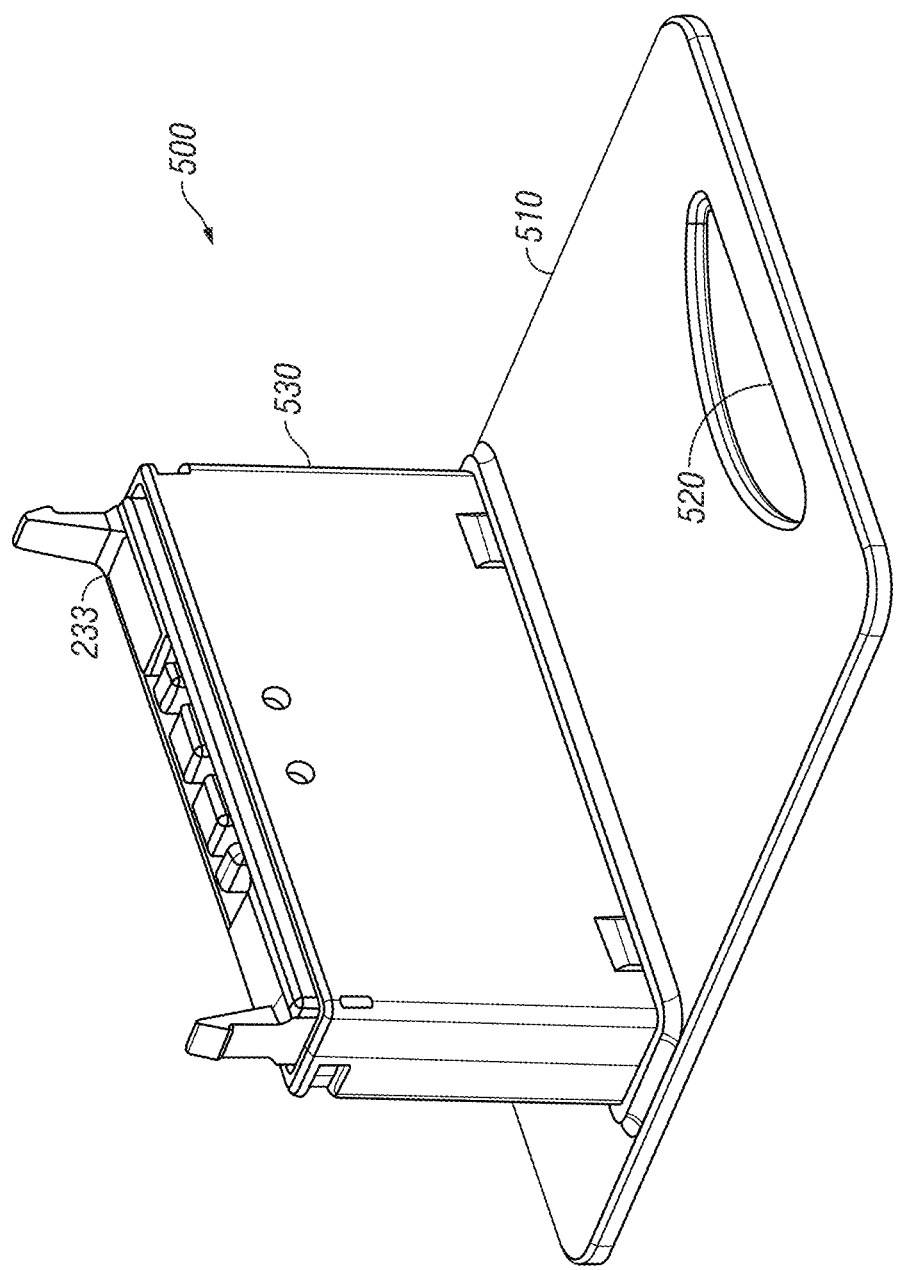
FIGS. 31-32 illustrate a docking member configured to receive the blade housing of the embodiment of FIGS. 21-23 in assembled and exploded views.
Figure 32:
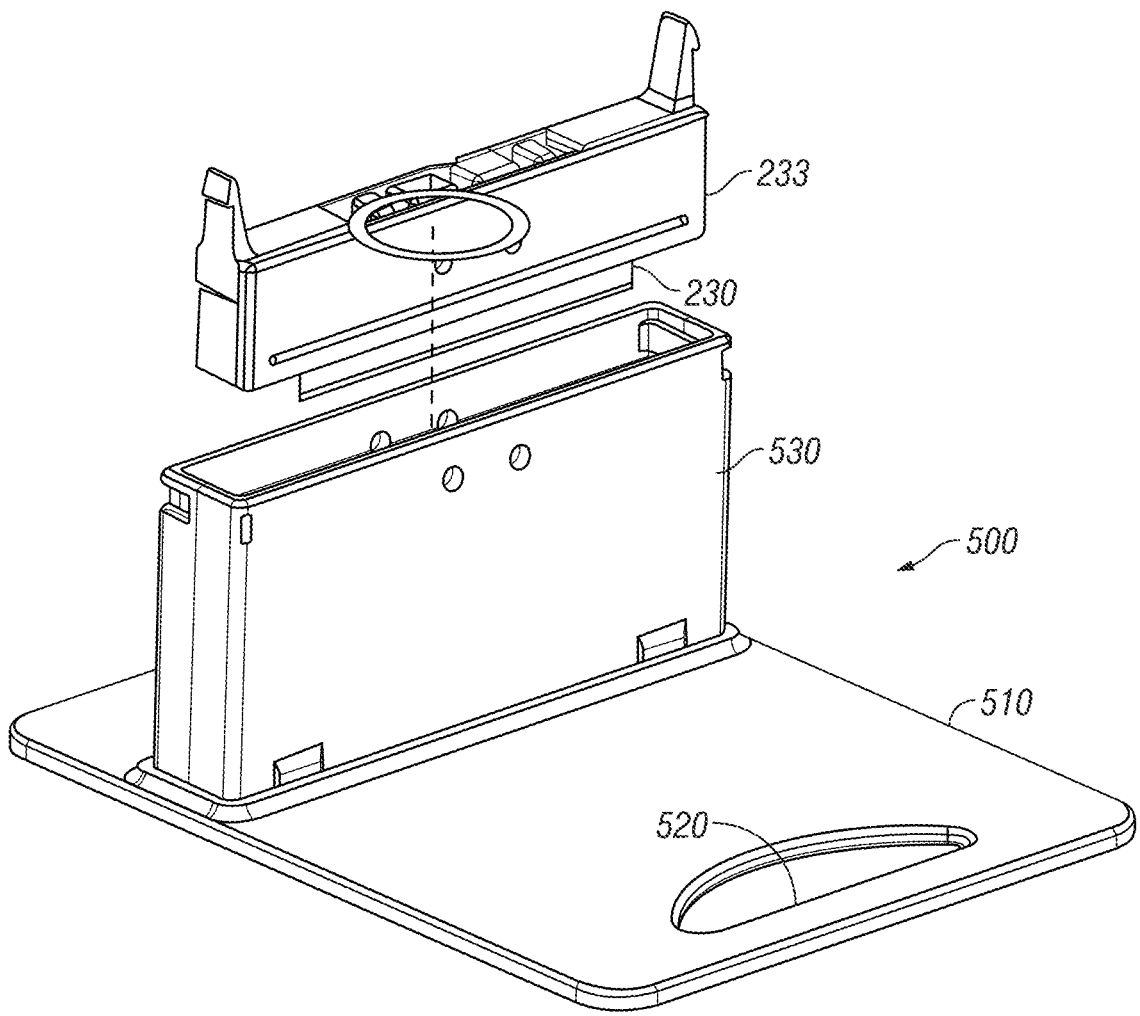
Figure 33:
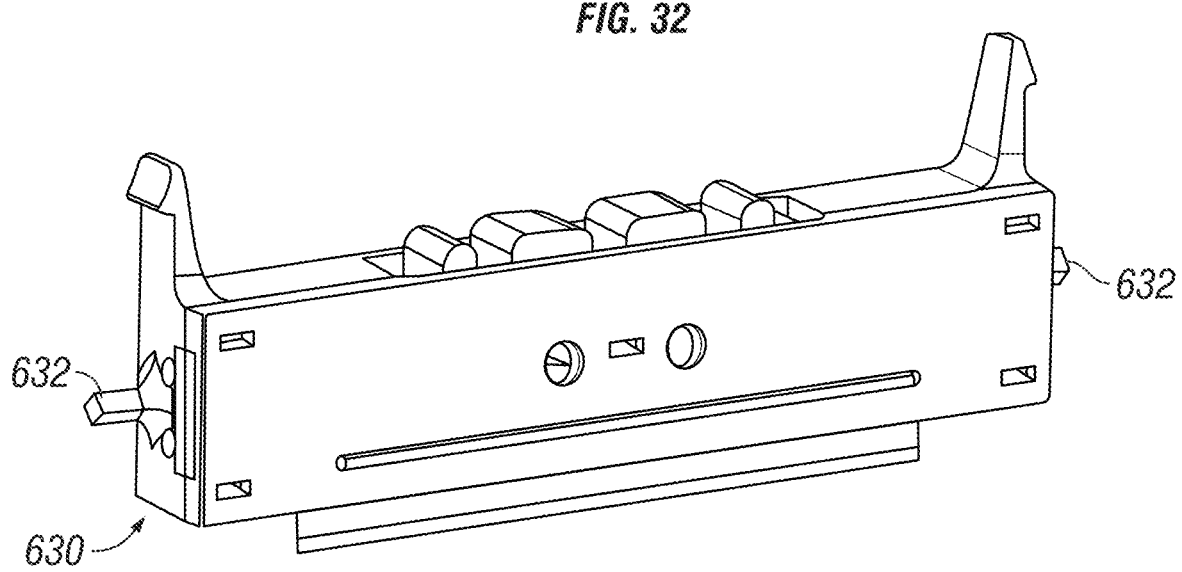
FIG. 33 illustrates an embodiment of a blade housing according to the present disclosure.

Referring now to FIGS. 31 and 32, a docking member 500 is configured to receive blade housing 233. Docking member 500 comprises a base portion 510 with handle 520 to provide convenient handling for the user. In addition, docking member 500 comprises a receptacle 530 that receives blade 230 and allows blade 230 to be safely stored for handling or shipping.

Figure 34:
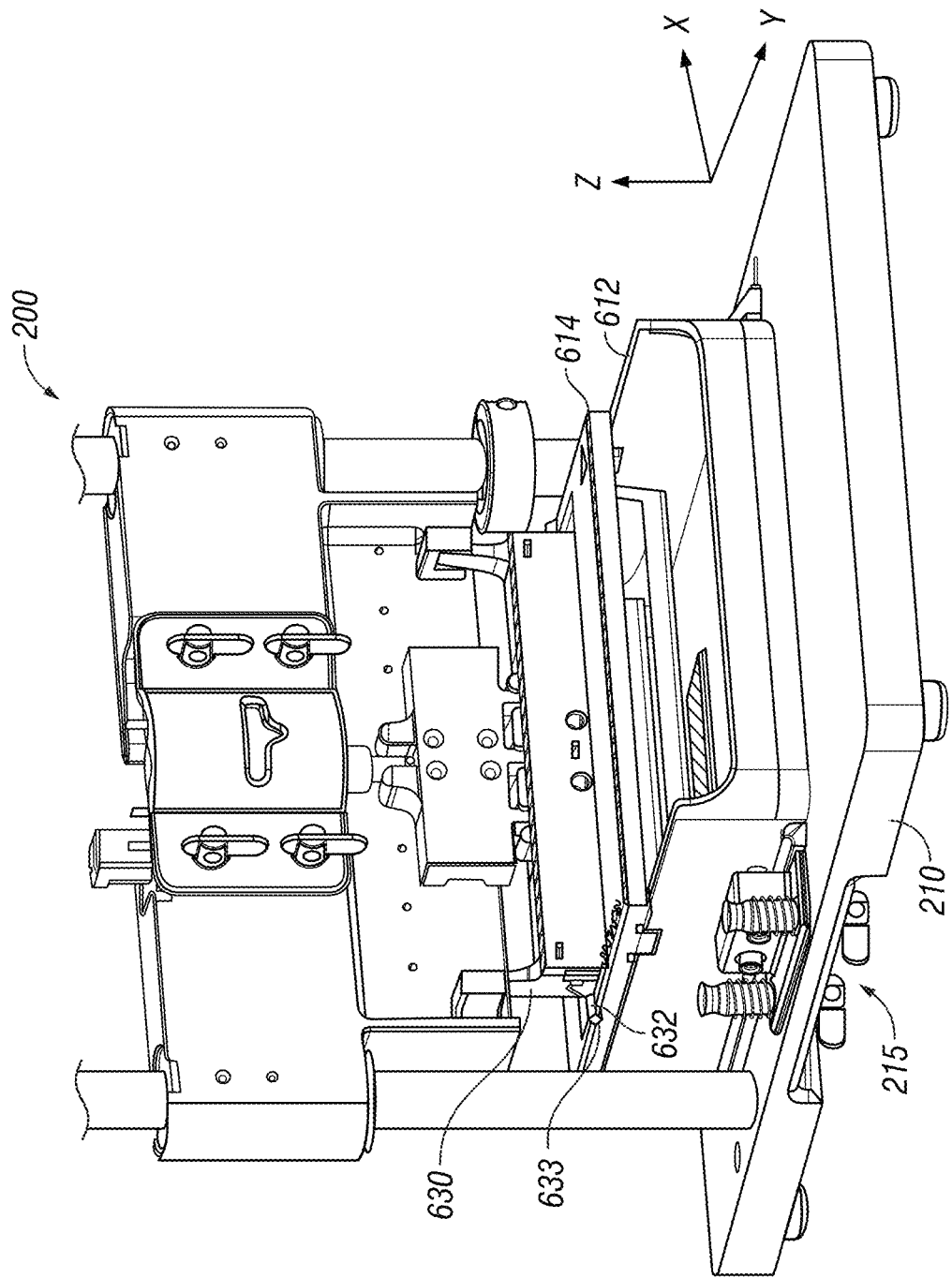
FIG. 34 illustrates an embodiment a patch harvester apparatus with the blade housing of FIG. 33.

FIGS. 33-36 illustrate a second embodiment of a blade housing 630 and associated components. In this embodiment, blade housing 630 comprises a pair of locating tabs 632 configured to locate blade housing 630 with respect to a lid 614 on a receptacle 612. Lid 614 includes a notch 633, such that the engagement of locating tab 632 with notch 633 restricts movement of blade housing 630 in the Y and Z directions during use as shown in FIG. 34. The embodiment shown in FIG. 34 further comprises a spring-loaded retaining mechanism 215 configured to couple receptacle 612 to base plate 210. Other operational aspects of this embodiment are equivalent to previously-described embodiments.

Figure 35:
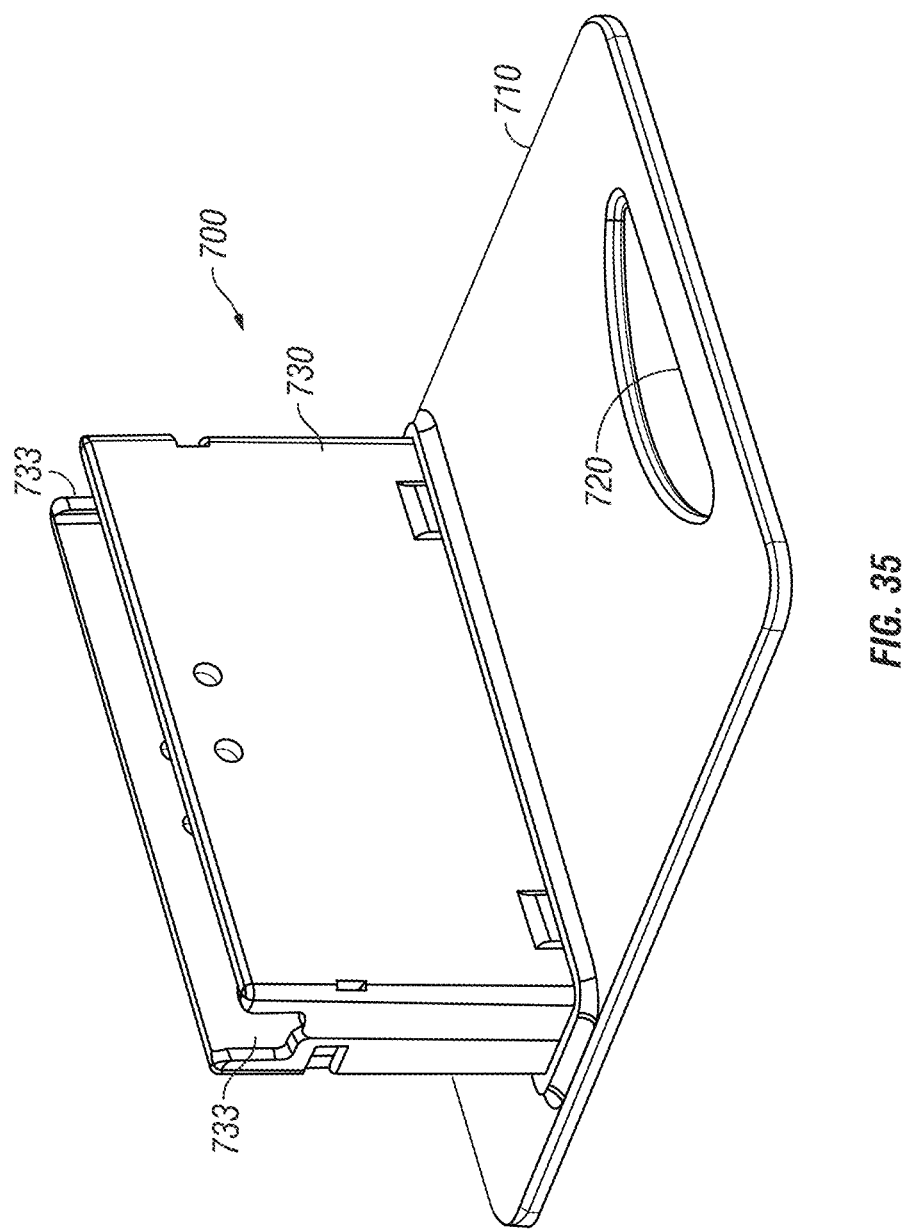
FIG. 35 illustrates a docking member configured to receive the blade housing of the embodiment of FIG. 33.
Figure 36:
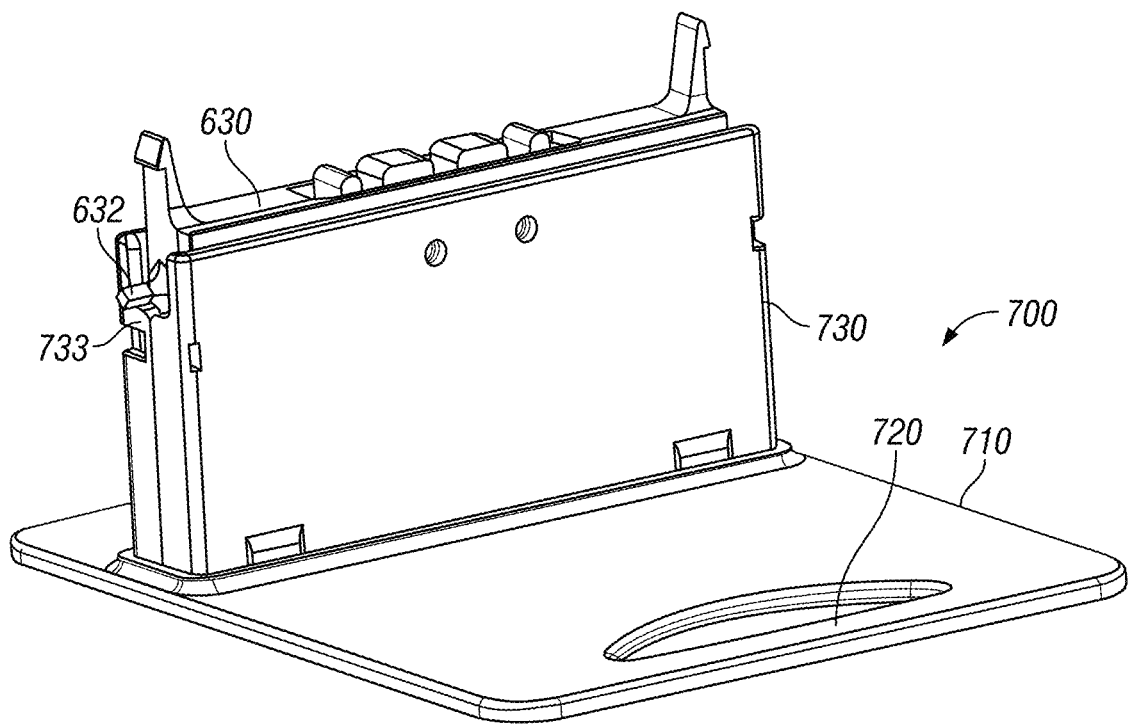
FIG. 36 illustrates the blade housing of the embodiment of FIG. 33 inserted into the docking member of the embodiment of FIG. 35.

As shown in FIG. 35, docking member 700 is similarly configured to previously-described docking station 500. Docking member 700 comprises a base portion 710 with handle 720 to provide convenient handling for the user. In addition, docking member 700 comprises a receptacle 730 with blade notches 733 to accommodate tabs 632 during storage of blade housing 630.

* * * * * * * * * * * * *

It should be observed that while the foregoing detailed description of various embodiments of the present invention is set forth in some detail, the invention is not limited to those details and devices, kits and methods according to the invention can differ from the disclosed embodiments in numerous ways. It will be appreciated that the functions disclosed herein as being performed by particular embodiments may be performed differently in an alternative embodiment. It should be further noted that functional distinctions are made above for purposes of explanation and clarity; structural distinctions in a system or method according to the invention may not be drawn along the same boundaries. Hence, the appropriate scope hereof is deemed to be in accordance with the claims as set forth below.

REFERENCES

The following references, to the extent that they provide exemplary procedural or other details supplementary to those set forth herein, are specifically incorporated herein by reference.

U.S. Pat. Nos. 5,919,702; 8,900,863; and 9,012,222
United States Patent Publication 2008/0118477
United States Patent Publication 2011/0151556
United States Patent Publication 20130072951
United States Patent Publication 2013/0183273
United States Patent Publication 20140120615
U.S. patent application Ser. No. 15/449,085
PCT Publication WO/2008/060037A1
PCT Publication WO/2011/101834
Stem Cell Res Ther. 2015 Mar. 19; 6:38. doi: 10.1186/s13287-015-0031-3.
PLoS One. 2014 Oct. 20; 9(10):e110764. doi: 10.1371/journal.pone.0110764. eCollection 2014.
Stem Cell Res Ther. 2014 May 2; 5(3):62. doi: 10.1186/scrt451.
Int J Mol Sci. 2013 May 31; 14(6):11692-712. doi: 10.3390/ijms140611692.
Int Rev Neurobiol. 2013; 108:79-120. doi: 10.1016/B978-0-12-410499-0.00004-6.
Neural Regen Res. 2013 Jul. 5; 8(19): 1783-1792.
Placenta. 2011 October; 32 Suppl 4:S311-5. doi: 10.1016/j.placenta.2011.06.010. Epub 2011 Jul. 6.
Tissue Engineering Part A (Impact Factor: 4.64). June 2011; 17(21-22):2651-61. DOI: 10.1089/ten.TEA.2010.0587.
Stem Cell Rev. 2010 March; 6(1):15-26. doi: 10.1007/s12015-009-9102-0.
Tissue Eng Part A. 2009 September; 15(9):2325-34. doi: 10.1089/ten.tea.2008.0402.
Haematologica. 2006 August; 91(8):1017-26. Epub 2006 Jul. 25.

What is claimed is:

1. A method of harvesting a patch from an umbilical cord, the method comprising:
    obtaining an apparatus for processing an umbilical cord, the apparatus comprising:
        a base plate assembly, wherein the base plate assembly has a planar surface;
        a bar coupled to the base plate assembly, wherein the bar is spaced from the planar surface such that a first gap exists between the bar and the planar surface;
        a motor coupled to the base plate assembly, wherein:
        the motor comprises a shaft with an eccentric pinion; and
        the shaft with the eccentric pinion is generally perpendicular to the bar; and
        a reciprocating blade coupled to the motor, wherein:
        the reciprocating blade comprises a cutting edge that is parallel to the bar; and
        a second gap exists between the cutting edge and the bar;
    inserting one end of an umbilical cord between the planar surface of the base plate and the bar;
    wrapping the umbilical cord around the bar;
    pulling the first end of the umbilical cord away from the bar; and
    engaging the reciprocating blade with the umbilical cord to cut a patch from the umbilical cord.

2. The method of claim 1 wherein:
    engaging the umbilical cord comprises operating the motor to move the reciprocating blade back and forth above the bar.

3. The method of claim 1 wherein the bar exerts a frictional resistance force when the first end of the umbilical cord is pulled away from the bar.

4. The method of claim 1 further comprising adjusting the first gap between the bar and the planar surface.

5. The method of claim 4 wherein adjusting the first gap between the bar and the planar surface comprises replacing the bar coupled to the base plate assembly with a different bar that is spaced from the planar surface a different gap than the first gap.

6. The method of claim 1 wherein the patch comprises Wharton's Jelly and amnion.

7. The method of claim 1 wherein the patch does not comprise umbilical arteries.

8. The method of claim 1 wherein the umbilical cord has been processed to remove a blood vessel before harvesting the patch from the umbilical cord.

9. The method of claim 8 wherein the umbilical cord has been processed by:
   obtaining a device comprising a handle coupled to a tapered rod and coupled to a blade, wherein the blade is spaced apart from the tapered rod;
   inserting the tapered rod into a lumen of the blood vessel of the umbilical cord; and
   cutting the umbilical cord along a length of the umbilical cord with the blade.

10. The method of claim 9 wherein the tapered rod and blade are positioned such that:
    a radial space exists between the tapered rod and the blade;
    the blade cuts the umbilical cord along a length of the umbilical cord when the tapered rod is inserted into the lumen of the blood vessel in the umbilical cord; and
    the blade does not cut the blood vessel in umbilical cord when the tapered rod is inserted into the lumen of the blood vessel in the umbilical cord.

11. The method of claim 10 further comprising compressing the blood vessel of the umbilical cord on the tapered rod without cutting the blood vessel of the umbilical cord.

12. The method of claim 11 further comprising pulling the umbilical cord along the tapered rod and toward the handle.

13. The method of claim 11 further comprising using forceps to pull the umbilical cord along the tapered rod and toward the handle.

14. The method of claim 8 wherein the blood vessel of the umbilical cord is an umbilical vein.

* * * * *